US011702453B2

(12) United States Patent
Tai et al.

(10) Patent No.: US 11,702,453 B2
(45) Date of Patent: Jul. 18, 2023

(54) MATERIALS AND METHODS FOR INHIBITING FLAVIVIRUS INFECTION

(71) Applicant: THE REGENTS OF THE UNIVERSITY OF MICHIGAN, Ann Arbor, MI (US)

(72) Inventors: Andrew Tai, Ann Arbor, MI (US); David Lin, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/269,191

(22) PCT Filed: Aug. 20, 2019

(86) PCT No.: PCT/US2019/047260
§ 371 (c)(1),
(2) Date: Feb. 17, 2021

(87) PCT Pub. No.: WO2020/041309
PCT Pub. Date: Feb. 27, 2020

(65) Prior Publication Data
US 2021/0269490 A1 Sep. 2, 2021

Related U.S. Application Data

(60) Provisional application No. 62/720,599, filed on Aug. 21, 2018.

(51) Int. Cl.
| | | |
|---|---|---|
| C07K 14/18 | (2006.01) | |
| A61P 31/14 | (2006.01) | |
| A61K 31/7052 | (2006.01) | |
| C07H 21/04 | (2006.01) | |
| A61K 38/00 | (2006.01) | |

(52) U.S. Cl.
CPC ...... *C07K 14/1825* (2013.01); *A61K 31/7052* (2013.01); *A61P 31/14* (2018.01); *C07H 21/04* (2013.01); *A61K 38/00* (2013.01); *C07K 2319/91* (2013.01); *C12N 2770/24122* (2013.01)

(58) Field of Classification Search
None
See application file for complete search history.

(56) References Cited

U.S. PATENT DOCUMENTS

| | | |
|---|---|---|
| 2006/0062803 A1 | 3/2006 | Kinney et al. |
| 2009/0117149 A1 | 5/2009 | Wicker et al. |
| 2012/0070454 A1 | 3/2012 | Lin |
| 2016/0317644 A1 | 11/2016 | Smith et al. |
| 2017/0037379 A1 | 2/2017 | Palese et al. |
| 2018/0036398 A1 | 2/2018 | Hagen et al. |

FOREIGN PATENT DOCUMENTS

WO  WO-2017/140905 A1  8/2017

OTHER PUBLICATIONS

Freire et al., "Mapping Putative B-Cell Zika Virus NS1 Epitopes Provides Molecular Basis for Anti-NS1 Antibody Discrimination between Zika and Dengue Viruses," ACS Omega 2(7):3913-3920 (2017).
Huang et al., "The dengue virus type 2 envelope protein fusion peptide is essential for membrane fusion," Virology 396:305-15 (2010).
International Search Report and Written Opinion from International Application No. PCT/US2019/047260 dated Nov. 25, 2019.
Ito et al., "Transgenic anopheline mosquitoes impaired in transmission of a malaria parasite," Nature 417(6887):452-455 (2002).
Lanciotti et al., "Phylogeny of Zika Virus in Western Hemisphere, 2015," Emerg Infect Dis 22:933-5 (2016).
Lin et al., "Dengue Virus Hijacks a Noncanonical Oxidoreductase Function of a Cellular Oligosaccharyltransferase Complex," MBio 8(4):e00939-17, 16 pages (2017).
Muylaert et al., Mutagenesis of the N-Linked Glycosylation Sites of the Yellow Fever Virus NS1 Protein: Effects on Virus Replication and Mouse Neurovirulence, Virology 222:159-168 (1996).
Salloum et al., "Rab18 binds to hepatitis C virus NS5A and promotes interaction between sites of viral replication and lipid droplets," PLoS Pathog 9:e1003513, 16 pages (2013).
Schoggins et al., "Dengue reporter viruses reveal viral dynamics in interferon receptor-deficient mice and sensitivity to interferon effectors in vitro," Proc Natl Acad Sci U S A 109:14610-5 (2012).

(Continued)

*Primary Examiner* — Stacy B Chen
(74) *Attorney, Agent, or Firm* — Marshall, Gerstein & Borun LLP

(57) ABSTRACT

The disclosure provides materials in the form of flavivirus variants that each encode a Non-Structural Protein-1 (NS1) variant, wherein the coding region is a chimera of at least two different NS1 coding regions, or wherein the coding region has at least one mutation in a codon of a canonical Asn-Xxx-Ser/Thr N-linked glycosylation site, wherein Asn is asparagine, Xxx is any amino acid, and Ser/Thr is either serine or threonine, or wherein the coding region is both a chimera and has at least one mutation in a codon of a canonical N-liked glycosylation site, wherein Asn is asparagine, Xxx is any amino acid, and Ser/Thr is either serine or threonine. The disclosure also provides methods of using such flavivirus variants to inhibit the transmission of infectious flavivirus.

25 Claims, 12 Drawing Sheets
Specification includes a Sequence Listing.

(56) References Cited

OTHER PUBLICATIONS

Tsetsarkin et al., "A Full-Length Infectious cDNA Clone of Zika Virus from the 2015 Epidemic in Brazil as a Genetic Platform for Studies of Virus-Host Interactions and Vaccine Development," MBio 7(4):8 pages (2016).

Yamamoto et al., "Flying vaccinator; a transgenic mosquito delivers a Leishmania vaccine via blood feeding," Insect Molecular Biology 19(3):391-398 (2010).

Yi et al., "Identification and characterization of the host protein DNAJC14 as a broadly active flavivirus replication modulator," PLoS Pathog 7:e1001255, 18 pages (2011).

MATERIALS AND METHODS FOR INHIBITING FLAVIVIRUS INFECTION

CROSS-REFERENCE TO RELATED APPLICATIONS

This application is a U.S. National Phase of PCT/US19/47260, filed Aug. 20, 2019, which claims priority to U.S. Provisional Patent Application No. 62/720,599, filed Aug. 21, 2018, which is hereby incorporated by reference in its entirety.

STATEMENT OF GOVERNMENT SUPPORT

This invention was made with government support under DK097374 awarded by the National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 52941A_Seqlisting.txt; 15,459 bytes, created Aug. 19, 2019.

FIELD

The disclosure relates generally to the field of viral infection and more particularly to flavivirus infection.

BACKGROUND

Many members of the genus Flavivirus cause significant morbidity and mortality in humans. Several that cause disease in humans are transmitted by an arthropod vector (mosquitos or ticks), including dengue, Zika, yellow fever, West Nile, Japanese encephalitis, and St. Louis encephalitis viruses. Dengue alone has been estimated to cause up to 390 million acute infections worldwide each year. There are no effective antiviral therapies against any flavivirus, and vaccines have been developed against only a few flaviviruses, such as yellow fever and Japanese encephalitis virus. All flaviviruses encode a protein called NS1 that is essential for viral replication. All three of these viruses are transmitted by *Aedes aegypti* and *Aedes albopictus* mosquitos, but primarily by *A. aegypti*.

Recently, Australian scientists at the Commonwealth Scientific and Industrial Research Organization and at James Cook University conducted an experiment using the Sterile Insect Technique approach to inhibit disease transmission by mosquito vectors. In the laboratory, 20 million male *Aedes aegypti* mosquitos were infected with bacteria that led to their sterilization. Three million sterilized *A. aegypti* mosquitos were subsequently released, leading to an 80% reduction in disease-bearing *A. aegypti* mosquitos in the areas of release. The experiment demonstrates success in attacking vectors of disease, but it is unclear what the ratio of healthy to sterile male mosquitos was in the release areas and whether under different conditions the sterile males could successfully compete with healthy males for breeding opportunities.

In view of the foregoing observations, a need continues to exist in the art for methods of inhibiting the transmission of infectious flaviviruses and for methods of vaccinating subjects against such infections.

SUMMARY

In addition to antivirals and human vaccines, a strategy to reduce the incidence of flavivirus infection would be to interrupt transmission by its arthropod vectors. Dengue, Zika, and yellow fever viruses, for example, are all transmitted by mosquitos of the *Aedes* genus, chiefly *A. aegypti* but also *A. albopictus*. All flaviviruses encode a protein called NS1 that is essential for viral replication as well as for virion assembly. The NS1 protein is synthesized in the endoplasmic reticulum (ER) of the infected cell. Upon translocation into the ER lumen, it rapidly dimerizes and is N-glycosylated at two or three sites, depending on the virus.

The disclosure provides polynucleotide coding regions for flavivirus NS1 protein variants, and the protein variants themselves. The NS1 protein variants of the disclosure include flavivirus NS1 chimeras comprising fragments of at least two distinct flavivirus NS1 proteins, with the distinct NS1 proteins being derived from different flavivirus serotypes (e.g., Dengue fever virus serotype 1, 2, 3, or 4) or different flavivirus species (e.g., Dengue fever virus, Zika virus, Yellow fever virus). The materials according to the disclosure are useful in reducing the ability of infectious flavivirus to infect the mosquito vector, thereby reducing the risk of flavivirus infection in animals such as man.

The chimeric NS1 proteins may exhibit 1:1 sequence correspondence, but not sequence, to one or more naturally occurring (e.g., wild-type) flaviviruses, or the NS1 chimeric protein variant may exhibit one or more deletions or insertions of 1, 2, 3, 4, 5, 6, 7, 8, 9, 10 or more amino acids relative to the sequence of a naturally occurring flavivirus NS1 protein. The NS1 protein variants of the disclosure, and the encoding polynucleotides, may comprise a mutation that alters at least one canonical sequence of an N-linked glycosylation site, i.e., asparagine-any amino acid-serine or threonine (Asn-X-Ser/Thr, where X is any amino acid) in a flavivirus NS1 protein. Contemplated by the disclosure are non-silent missense mutations that substitute a non-asparagine amino acid for an asparagine amino acid participating in a canonical N-linked glycosylation site sequence. Other non-silent missense mutations according to the disclosure lead to the substitution in the Ser/Thr position of the canonical sequence, such that a non-serine amino acid is substituted for a serine or a non-threonine amino acid is substituted for a threonine. In addition to non-silent missense mutations leading to at least one amino acid substitution in a canonical N-linked glycosylation site, the disclosure provides for variants arising from at least one insertion or deletion that results in an alteration of the amino acid sequence of at least one N-linked glycosylation site. The disclosure contemplates flavivirus NS1 protein variants comprising at least one mutation that locally alters the native or wild-type sequence of a flavivirus NS1 amino acid sequence around at least one canonical sequence for a N-linked glycosylation site without significantly altering the remainder of the NS1 amino acid sequence. An exemplary flavivirus NS1 protein variant is a mutant of the Zika virus NS1 protein that results in substitution of an alanine for an asparagine corresponding to position 130 (N130A), which is within a canonical Asn-X-Ser/Thr N-linked glycosylation site in wild-type Zika virus NS1 protein. An expressible polynucleotide encoding the Zika virus NS1 protein variant is capable of potently blocking infection by Dengue fever virus, Zika virus, and Yellow fever virus in cell culture. Engineered *Aedes* mosquitos expressing such NS1 mutants transgenically are incapable of transmitting these flaviviruses, and are suitable for release to breed with wild-type *Aedes* mosquitos to disseminate the coding region for the NS1 protein variant.

The disclosure also provides flavivirus NS1 protein variants and coding regions therefor that exhibit altered glycosylation. In describing the flavivirus NS1 protein variants according to the disclosure, a modified amino acid or a modification of an amino acid is expressly defined to mean a deletion of that amino acid, a substitution of that amino acid with one or more different amino acids, or an insertion of one or more amino acids that disrupts a canonical N-linked glycosylation site. In particular, the disclosure comprehends flavivirus NS1 proteins such as the Zika NS1 protein mutated, i.e., modified, at position 130, which is an Asn residue in the wild-type Zika NS1 protein, or at a position corresponding to position 130 in wild-type Zika NS1 protein. N-linked glycosylation involves glycan modification of an asparagine residue. The canonical N-linked glycosylation site in a protein is Asn-Xxx-Ser/Thr, where Xxx is any amino acid and Ser/Thr refers to a serine or threonine residue at, or corresponding to, the indicated position. For N-linked glycosylation of the Zika virus NS1 protein, the N-linked glycosylation site spans amino acids 130-132, i.e., the Asn-Asn-Ser sequence of SEQ ID NO:2. Contemplated are variants that prevent the N-linked glycosylation at, or at a position corresponding to, the Asn130 characteristic of wild-type Zika NS1. Accordingly, modification of Asn130, modification of Asn131, modification of Ser132, modification of Asn130 and Asn131, modification of Asn130 and Ser132, modification of Asn131 and Ser132, and modification of Asn130, Asn131 and Ser132 in Zika virus NS1 are contemplated NS1 variants useful according to the disclosure, as are modifications of the amino acids in these canonical N-linked glycosylation sites in NS1 of any Zika virus serotype that correspond to the indicated N-linked glycosylation site at positions 130-132 of SEQ ID NO:2. Moreover, substitution of Asn130, or Asn at a position corresponding to Asn130, with any other amino acid and/or substitution of Ser132, or a Ser at a position corresponding to Ser132, with any amino acid other than threonine are contemplated NS1 variants according to the disclosure.

Mutations at N-linked glycosylation sites in the NS1 protein of other flaviviruses, including any N-linked glycosylation sites at positions corresponding to the Asn-Asn-Ser at positions 130-132 of Zika virus NS1, are NS1 variants according to the disclosure. Dengue fever NS1 has two N-linked glycosylation sites, i.e., the Asn-Xxx-Thr sequence that corresponds to positions 130-132 of SEQ ID NO:4, which is Asn-Gln-Thr in Dengue fever NS1 serotype 2, and the Asn-Xxx-Thr sequence that corresponds to positions 207-209 of SEQ ID NO:4, which is Asn-Asp-Thr in Dengue fever NS1 serotype 2. For the Dengue fever NS1 protein, modification of Asn130, modification of Gln131, modification of Thr132, modification of Asn130 and Gln131, modification of Asn130 and Thr132, modification of Gln131 and Thr132, and modification of Asn130, Gln131 and Thr132 in Dengue fever virus NS1 are contemplated NS1 variants, as are modifications of the amino acids in this canonical N-linked glycosylation site in NS1 of any Dengue fever virus serotype that correspond to the indicated N-linked glycosylation site at positions 130-132 of SEQ ID NO:4. In addition, modification of Asn207, modification of Asp208, modification of Thr209, modification of Asn207 and Asp208, modification of Asn207 and Thr209, modification of Asp208 and Thr209, and modification of Asn207, Asp208 and Thr209 in Dengue fever virus NS1 are contemplated NS1 variants useful according to the disclosure, as are modifications of the amino acids in this canonical N-linked glycosylation site in NS1 of any Dengue fever virus serotype that correspond to the indicated N-linked glycosylation site at positions 207-209 of SEQ ID NO:4. Given the presence of two N-linked glycosylation sites in Dengue fever NS1, the disclosure contemplates any combination of modifications of amino acid residues in each of the N-linked glycosylation sites. Thus, the disclosure comprehends Dengue fever NS1 variants comprising a modified Asn130 and Asn207, a modified Asn130 and Asp208, a modified Asn130 and Thr209, a modified Asn130, Asn207 and Asp208, a modified Asn130, Asn207 and Thr209, a modified Asn130, Asp208 and Thr209, a modified Asn130, Asn207, Asp208 and Thr209, a modified Gln131 and Asn207, a modified Gln131 and Asp208, a modified Gln131 and Thr209, a modified Gln131, Asn207 and Asp208, a modified Gln131, Asn207 and Thr209, a modified Gln131, Asp208 and Thr209, a modified Gln131, Asn207, Asp208 and Thr209, a modified Thr132 and Asn207, a modified Thr132 and Asp208, a modified Thr132 and Thr209, a modified Thr132, Asn207 and Asp208, a modified Thr132, Asn207 and Thr209, a modified Thr132, Asp208 and Thr209, and a modified Thr132, Asn207, Asp208 and Thr209, as are modifications of the amino acids in these canonical N-linked glycosylation sites in NS1 of any Dengue fever virus serotype that correspond to the indicated N-linked glycosylation site or sites at positions 130-132, 207-209, or to both 130-132 and 207-209 of SEQ ID NO:2.

Yellow fever NS1 also has two N-linked glycosylation sites, i.e., the Asn-Xxx-Ser sequence that corresponds to the Asn-Gly-Ser sequence at positions 130-132 of SEQ ID NO:6 and the Asn-Xxx-Gly sequence that corresponds to the Asn-Gly-Thr sequence at positions 208-210 of SEQ ID NO:6. For the Yellow fever NS1 protein, modification of Asn130, modification of Gly131, modification of Ser132, modification of Asn130 and Gly131, modification of Asn130 and Ser132, modification of Gly131 and Ser132, and modification of Asn130, Gly131 and Ser132 in Yellow fever virus NS1 are contemplated NS1 variants, as are modifications of the amino acids in these canonical N-linked glycosylation sites in NS1 of any Yellow fever virus serotype that correspond to the indicated N-linked glycosylation site at positions 130-132, 208-210, or to both 130-132 and 208-210 of SEQ ID NO:6. Also, modification of Asn208, modification of Gly209, modification of Thr210, modification of Asn208 and Gly209, modification of Asn208 and Thr210, modification of Gly209 and Thr210, and modification of Asn208, Gly209 and Thr210 in Yellow fever virus NS1 are contemplated NS1 variants useful according to the disclosure, as are modifications of the amino acids in these canonical N-linked glycosylation sites in NS1 of any Yellow fever virus serotype that correspond to the indicated N-linked glycosylation site at positions 130-132, 208-210, or to both 130-132 and 208-210 of SEQ ID NO:2. As for Dengue fever NS1 variants, the disclosure contemplates any combination of modifications of amino acid residues in each of the N-linked glycosylation sites of Yellow fever NS1. Thus, the disclosure comprehends Yellow fever NS1 variants comprising a modified Asn130 and Asn 235, a modified Asn130 and Gly209, a modified Asn130 and Thr210, a modified Asn130, Asn208 and Gly209, a modified Asn130, Asn208 and Thr210, a modified Asn130, Gly209 and Thr210, a modified Asn130, Asn208, Gly209 and Thr210, a modified Gly131 and Asn 235, a modified Gly131 and Gly209, a modified Gly131 and Thr210, a modified Gly131, Asn208 and Gly209, a modified Gly131, Asn208 and Thr210, a modified Gly131, Gly209 and Thr210, a modified Gly131, Asn208, Gly209 and Thr210, a modified Ser132 and Asn 235, a modified Ser132 and Gly209, a modified Ser132 and Thr210, a modified Ser132, Asn208 and Gly209, a modified Ser132, Asn208 and Thr210, a modified Ser132, Gly209 and Thr210, and a modified Ser132, Asn208, Gly209 and Thr210, as well as modifications of the amino acids in these canonical N-linked glycosylation sites in NS1 of any Yellow fever virus serotype that correspond to the indicated N-linked glycosylation site at positions 130-132, 208-210, or to both 130-132 and 208-210 of SEQ ID NO:2.

The disclosure provides flavivirus NS1 variants that disrupt an N-linked glycosylation site. Apparent from this disclosure is that NS1 variants of the disclosure that comprise one or more modified amino acids at positions corresponding to a reference N-linked glycosylation site or sites include embodiments in which the modified amino acids are at the referenced positions of the N-linked glycosylation site or sites.

The disclosure also provides methods of using the products described above. One method involves reducing the risk of flavivirus infection by introducing a transgenic coding region for an expressible flavivirus NS1 protein variant into *Aedes* mosquitos and releasing the transgenic mosquitos in an area where breeding with wild-type *Aedes* mosquitos is likely, thereby disseminating the coding region for a flavivirus NS1 protein variant in the mosquito population and reducing the risk of flavivirus infection due to the inhibition of flavivirus infection of the mosquito vector that is provided by the NS1 protein variant, as disclosed herein. Because the transgenic mosquitos cannot be productively infected by infectious flaviviruses, the risk of infection from such a vector is reduced. An exemplary embodiment of the method focuses on expressing the mutant Asn130Ala Zika NS1 protein in *Aedes* mosquitos transgenically. The Asn130Ala Zika NS1 protein variant is an NS1 protein variant according to the disclosure that is described in greater detail hereinbelow. Such a transgenic mosquito expressing the mutant Asn130Ala Zika NS1 protein is expected to be resistant to infection by Zika, Dengue fever, and Yellow fever virus. Consequently, such mosquitos would be incapable of transmitting these flaviviruses upon release into the wild. These mosquitos are capable of breeding with the wild *Aedes* mosquito population, thereby disseminating the mutant NS1 allele in the endemic mosquito population. The disclosure comprehends additional flavivirus NS1 protein variants and coding regions therefor, wherein the NS1 protein variants exhibit at least one modified N-linked glycosylation site, as well as methods of reducing the risk of flavivirus by administering such products to a mosquito vector (e.g., an *Aedes* mosquito) and breeding such mosquitos to spread the inhibitory allele in an arthropod vector, such as a mosquito vector like the *Aedes* mosquito.

In one aspect, the disclosure provides a coding region for a Non-Structural Protein-1 (NS1) variant, wherein the coding region is a chimera of at least two different NS1 coding regions, or wherein the coding region has at least one mutation in a codon of a canonical Asn-Xxx-Ser/Thr N-linked glycosylation site, wherein Asn is asparagine, Xxx is any amino acid, and Ser/Thr is either serine or threonine, or wherein the coding region is both a chimera and has at least one mutation in a codon of a canonical N-liked glycosylation site. In a related aspect, the disclosure provides a coding region for a Non-Structural Protein-1 (NS1) variant, wherein the coding region is a chimera of at least two different NS1 coding regions or wherein the coding region is both a chimera and has at least one mutation in a codon of a canonical Asn-Xxx-Ser/Thr N-liked glycosylation site, wherein Asn is asparagine, Xxx is any amino acid, and Ser/Thr is either serine or threonine. In some embodiments, the chimera is a fusion of the NS1 coding regions of two flavivirus species, such as wherein the two flavivirus species are Dengue fever virus and Zika virus, Dengue fever virus and Yellow fever virus, or Zika virus and Yellow fever virus. In some embodiments, the fusion point of the chimera is within or immediately adjacent to a codon for asparagine found in a canonical N-linked glycosylation site sequence of Asn-Xxx-Ser/Thr. In some embodiments, the two flavivirus species are Dengue fever virus and Zika virus. In some embodiments, the NS1 chimera comprises N-terminal Zika virus NS1 amino acid sequence and C-terminal NS1 amino acid sequence from Dengue fever virus, or wherein the NS1 chimera comprises N-terminal Dengue fever virus NS1 amino acid sequence and C-terminal NS1 amino acid sequence from Zika virus, wherein the fusion point is at, or corresponds to, codon 130, 131, 132, 158, 159, 160, 235, 236 or 237. In some embodiments, the NS1 chimera comprises N-terminal Zika virus NS1 amino acid sequence and C-terminal NS1 amino acid sequence from Yellow fever virus, or wherein the NS1 chimera comprises N-terminal Yellow fever virus NS1 amino acid sequence and C-terminal NS1 amino acid sequence from Zika virus, wherein the fusion point is at, or corresponds to, codon 130, 131, 132, 208, 209, or 210. In some embodiments, the NS1 chimera comprises N-terminal Dengue fever virus NS1 amino acid sequence and C-terminal NS1 amino acid sequence from Yellow fever virus, or wherein the NS1 chimera comprises N-terminal Yellow fever virus NS1 amino acid sequence and C-terminal NS1 amino acid sequence from Dengue fever virus, wherein the fusion point is at, or corresponds to, codon 130, 131, 132, 158, 159, 160, 208, 209, 210, 235, 236, or 237. In some embodiments, the NS1 coding region is a chimera of more than two NS1 coding regions, such as wherein the chimera comprises different NS1 coding regions derived from different flavivirus species. In some embodiments, the chimera comprises different NS1 coding regions derived from different flavivirus serotypes. In some embodiments, the chimera comprises at least one insertion or at least one deletion compared to the wild-type coding region sequences of the chimera.

Some embodiments of the coding region disclosed herein provide a coding region for a Non-Structural Protein-1 (NS1) variant, wherein the mutation is a substitution of a non-asparagine codon for an asparagine codon. In some embodiments, the mutation is the deletion of at least one nucleotide in an asparagine codon. In some embodiments, the coding region is derived from Dengue fever virus, Zika virus or Yellow fever virus. In some embodiments, the coding region is derived from Dengue fever virus, including embodiments wherein the coding region comprises at least one codon substitution for at least one codon encoding the amino acids corresponding to, e.g., at, positions 130-132 of SEQ ID NO:4. In some embodiments, the coding region derived from Dengue fever virus comprises substitution of a codon encoding a non-asparagine amino acid for the codon encoding asparagine at or corresponding to position 130 of SEQ ID NO:4. In some of these embodiments, the non-asparagine amino acid is alanine. In some embodiments, the coding region derived from Dengue fever virus comprises substitution of a codon encoding an amino acid other than threonine for the codon encoding threonine at or corresponding to position 132 of SEQ ID NO:4. In some of these embodiments, the non-threonine amino acid is alanine. In some embodiments, the coding region derived from Dengue fever virus comprises a codon substitution at or corresponding to one or more codons encoding amino acids corresponding to positions 207-209 of SEQ ID NO:4, such as wherein the coding region comprises substitution of a non-asparagine codon for the asparagine codon encoding the amino acid at or corresponding to position 207 of SEQ ID NO:4. In some of these embodiments, the non-asparagine amino acid is alanine. In some embodiments, the coding region derived from Dengue fever virus comprises substitution of a codon encoding a non-threonine amino acid for the codon encoding threonine at or corresponding to position 209 of SEQ ID NO:4. In some of these embodiments, the non-threonine amino acid is alanine. In some embodiments, the coding region derived from Dengue fever virus comprises one of the following pairs of codon substitutions: (a) substitution of a non-asparagine codon for the codon encoding the asparagine at or corresponding to position 130 of SEQ ID NO:4 and substitution of a non-asparagine codon for the codon encoding the asparagine at or corresponding to position 207 of SEQ ID NO:4; (b) substitution of a non-asparagine codon for the codon encoding the asparagine at or corresponding to position 130 of SEQ ID NO:4 and substitution of a non-threonine codon for the codon encoding the threonine at or corresponding to position 209 of SEQ ID NO:4; (c) substitution of a non-threonine codon for the codon encoding the threonine at or corresponding to position 132 of SEQ ID NO:4 and substitution of a non-asparagine codon for the codon encoding the asparagine at or corresponding to position 207 of SEQ ID NO:4; or (d) substitution of a non-threonine codon for the codon encoding the threonine at or corresponding to position 132 of SEQ ID NO:4 and substitution of a non-threonine codon for the codon encoding the threonine at or corresponding to position 209 of SEQ ID NO:4.

In embodiments disclosed in this paragraph, the coding region is derived from Yellow fever virus. In some embodiments, the coding region comprises a codon substitution at one or more codons encoding amino acids at or corresponding to positions 130-132 of SEQ ID NO:6, such as wherein the coding region comprises substitution of a non-asparagine codon for the codon encoding the asparagine at or corresponding to position 130 of SEQ ID NO:6. In some of these embodiments, the non-asparagine amino acid is alanine. In some embodiments, the coding region comprises substitution of a non-serine codon for the codon encoding the serine at or corresponding to position 132 of SEQ ID NO:6. In some of these embodiments, the non-serine amino acid is alanine. In some embodiments, the coding region comprises a codon substitution at one or more codons encoding amino acids at or corresponding to positions 208-210 of SEQ ID NO:6, such as wherein the coding region comprises substitution of a non-asparagine codon for the codon encoding the asparagine at or corresponding to position 208 of SEQ ID NO:6. In some of these embodiments, the non-asparagine amino acid is alanine. In some embodiments, the coding region comprises substitution of a non-threonine codon for the codon encoding the threonine at or corresponding to position 210 of SEQ ID NO:6, such as wherein the non-asparagine amino acid is alanine. In some embodiments, the coding region derived from Yellow fever virus comprises one of the following pairs of codon substitutions: (a) substitution of a non-asparagine codon for the codon encoding the asparagine at or corresponding to position 130 of SEQ ID NO:6 and substitution of a non-asparagine codon for the codon encoding the asparagine at or corresponding to position 208 of SEQ ID NO:6; (b) substitution of a non-asparagine codon for the codon encoding the asparagine at or corresponding to position 130 of SEQ ID NO:6 and substitution of a non-threonine codon for the codon encoding the threonine at or corresponding to position 210 of SEQ ID NO:6; (c) substitution of a non-serine codon for the codon encoding the serine at or corresponding to position 132 of SEQ ID NO:6 and substitution of a non-asparagine codon for the codon encoding the asparagine at or corresponding to position 208 of SEQ ID NO:6; or (d) substitution of a non-serine codon for the codon encoding the serine at or corresponding to position 132 of SEQ ID NO:6 and substitution of a non-threonine codon for the codon encoding the threonine at or corresponding to position 210 of SEQ ID NO:6.

In embodiments disclosed in this paragraph, the coding region is derived from Zika virus. In some embodiments, the coding region comprises a codon substitution at one or more codons encoding amino acids at or corresponding to positions 130-132 of SEQ ID NO:2, such as wherein the coding region comprises substitution of a non-asparagine codon for the codon encoding the asparagine at or corresponding to position 130 of SEQ ID NO:2. In some of these embodiments, the non-asparagine amino acid is alanine. In some embodiments, the coding region comprises substitution of a non-serine codon for the codon encoding the serine at or corresponding to position 132 of SEQ ID NO:2, such as wherein the non-serine amino acid is alanine.

Another aspect of the disclosure is drawn to the NS1 protein variants that comprise a chimera of at least two different NS1 coding regions, or wherein the NS1 protein variant encoded by a coding region according to the disclosure has at least one mutation in a codon of a canonical Asn-Xxx-Ser/Thr N-linked glycosylation site, wherein Asn is asparagine, Xxx is any amino acid, and Ser/Thr is either serine or threonine, or wherein the NS1 protein variant is both a chimera and is encoded by a coding region that has at least one mutation in a codon of a canonical N-liked glycosylation site. In some embodiments, the NS1 protein variant is encoded by the coding region derived from Dengue fever virus, Yellow fever virus, or Zika virus or the NS1 protein variant is derived from a NS1 protein variant derived from Dengue fever virus, Yellow fever virus or Zika virus.

Another aspect of the disclosure is a method of reducing the risk of flavivirus infection in a subject comprising administering an effective amount of a coding region for a flavivirus NS1 protein variant, wherein the NS1 protein variant lacks at least one N-linked glycosylation site. A related aspect is drawn to a method of reducing the risk of flavivirus infection in a subject comprising administering an effective amount of a coding region for a flavivirus NS1 protein variant, wherein the coding region is a chimera of at least two different NS1 coding regions or wherein the coding region is both a chimera and has at least one mutation in a codon of a canonical Asn-Xxx-Ser/Thr N-linked glycosylation site, wherein Asn is asparagine, Xxx is any amino acid, and Ser/Thr is either serine or threonine. In some embodiments, the coding region for a flavivirus NS1 protein variant is derived from Dengue fever NS1 protein, Yellow fever NS1 protein, or Zika virus NS1 protein. In some embodiments, the risk of flavivirus infection is a risk of Dengue fever virus infection, Yellow fever virus infection, or Zika virus infection.

Yet another aspect of the disclosure is a method of reducing the risk of flavivirus infection in a population of humans comprising: (a) introducing a coding region for a flavivirus NS1 protein variant into a mosquito vector for flavivirus, wherein the NS1 protein variant lacks at least one N-linked glycosylation site; (b) breeding the mosquito vector; and (c) releasing the mosquito vector into an environment inhabited by humans, whereby the mosquito vector breeds with wild-type mosquitos of the same species, thereby disseminating the coding region for the NS1 protein variant to reduce the risk of flavivirus infection in the humans. A related aspect of the disclosure provides a method of reducing the risk of flavivirus infection in a population of humans comprising: (a) introducing a coding region, wherein the coding region is a chimera of at least two different NS1 coding regions or wherein the coding region is both a chimera and has at least one mutation in a codon of a canonical Asn-Xxx-Ser/Thr N-linked glycosylation site, wherein Asn is asparagine, Xxx is any amino acid, and Ser/Thr is either serine or threonine, into a mosquito vector for flavivirus; (b) breeding the mosquito vector; and (c) releasing the mosquito vector into an environment inhabited by humans, whereby the mosquito vector breeds with wild-type mosquitos of the same species, thereby disseminating the coding region for the NS1 protein variant to reduce the risk of flavivirus infection in the humans. In some embodiments, the coding region for the flavivirus NS1 protein variant is derived from the coding region for Dengue fever virus, Yellow fever virus, or Zika virus. In some embodiments, the risk of flavivirus infection is a risk of Dengue fever virus infection, Yellow fever virus infection, or Zika virus infection.

Other features and advantages of the disclosure will be better understood by reference to the following detailed description, including the drawing and the examples.

BRIEF DESCRIPTION OF THE DRAWINGS

FIG. 6. Dengue virus variants, I.e., DENV N207A and N130A/N207A mutants, block DENV-2 Infection. Assay for Renilla luciferase expression from reporter Dengue virus construct in cells expressing the indicated Dengue fever NS1 variant or in control Huh7.5.1 cells. The histogram shows the level of Renilla luciferase expression in Relative Light Units (RLU) from cells containing the vector used to introduce DENV-2 variants, the wild-type NS1 or the indicated NS1 single or double variant. The middle panels shows an immunoblot for the NS1-flag protein (DYKDDDDK, SEQ ID NO:7) in lysates from each cell type identified along the x-axis of the histogram, and the bottom panel is a control immunoblot for actin expression in the same cell types. Vec is vector, WT is wild-type, N130A is a substitution of Alanine for Asparagine at position 130 of the relevant amino acid sequence, and N207A is a substitution of an Alanine for Asparagine at position 207 of the relevant amino acid sequence.

FIG. 7. Zika virus variants, I.e., ZIKV N130A and N130A/N207A mutants, block DENV-2 Infection. Assay for Renilla luciferase expression from reporter Dengue virus construct in cells expressing the indicated Zika virus NS1 variant or in control Huh7.5.1 cells. The histogram shows the level of Renilla luciferase expression in Relative Light Units (RLU) from cells containing the vector used to introduce Zika virus variants, the wild-type Zika virus NS1 or the indicated Zika virus NS1 single or double variant. The middle panel shows an immunoblot for the NS1-flag protein in lysates from each cell type identified along the x-axis of the histogram, and the bottom panel is a control immunoblot for actin expression in the same cell types.

FIG. 8. ZIKV N130A mutant blocks DENV-2 (Dengue fever virus), YFV (Yellow fever virus), and ZIKV (Zika virus) Infection. Infection assays were performed to assess the protective effects of Zika virus NS1 variants against infection by various flaviviruses, i.e., Dengue fever virus, Yellow fever virus and Zika virus.

DETAILED DESCRIPTION

Figure 1:
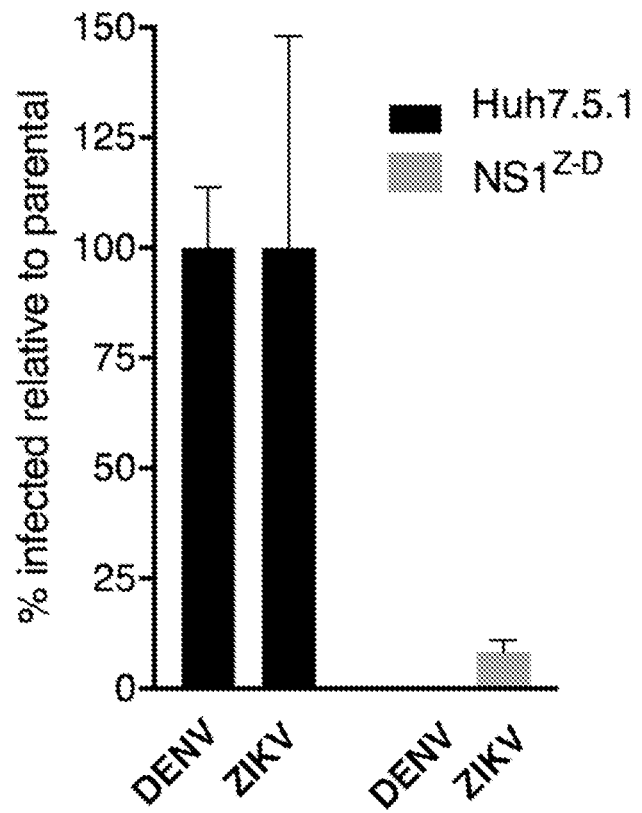
FIG. 1. Chimeric flavivirus variants. The percent of Huh7.5.1 cells expressing a Zika virus NS1-Dengue fever virus NS1 chimera ($NS1^{Z-D}$: Z-D chimera with the junction at amino acid 130) that were infected by wild-type Zika virus (ZIKV) or wild-type Dengue fever virus (DENV) relative to the level of infection of Huh7.5.1 cells not expressing a NS1 chimera by each wild-type virus were determined and plotted as a histogram.
Figure 2:
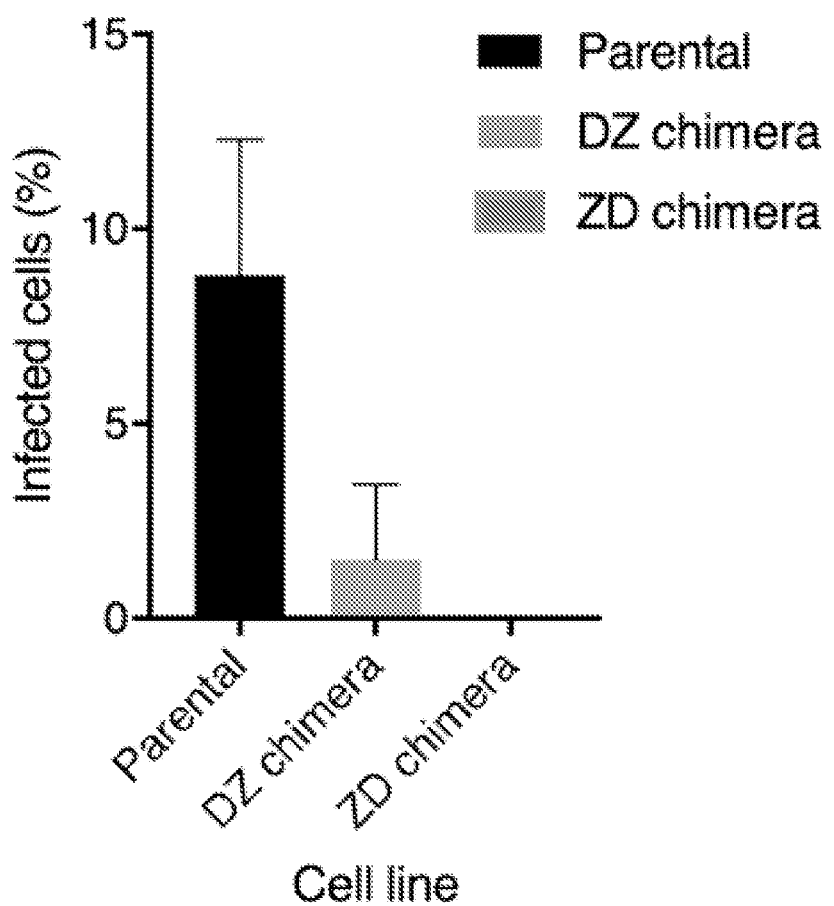
FIG. 2. Chimeric flavivirus variants. The percent of Huh7.5.1 cells expressing either a Dengue fever Virus NS1-Zika virus NS1 chimera (DZ chimera with the junction at amino acid 130) or a Zika virus NS1-Dengue fever virus NS1 chimera (ZD chimera with the junction at amino acid 130) that were infected by wild-type Zika virus relative to the level of infection of Huh7.5.1 cells not expressing a NS1 chimera by the wild-type virus were determined and plotted as a histogram.

The disclosure provides flavivirus NS1 variants useful in blocking infection by flaviviruses, including Dengue fever virus, Zika virus and Yellow fever virus. The flavivirus variants comprise a mutated coding region for the Non-Structural Protein 1, or NS1, of one or more flaviviruses. The NS1 variant coding regions include coding regions in which a part of the NS1 coding region of a given flavivirus is substituted by a generally or specifically corresponding part of the NS1 coding region of a different flavivirus, which may be a different serotype of a given flavivirus (e.g., Dengue fever virus serotype 1, 2, 3, or 4), or from a different flavivirus species, such as chimeras between the NS1 coding regions of Dengue fever virus and Zika virus, Yellow fever virus, or another flavivirus species. The chimera may encode an apparently full-length NS1 protein that exhibits 1:1 correspondence to the amino acid sequence of a wild-type flavivirus NS1 protein. Other chimeras according to the disclosure may not map using 1:1 correspondence to wild-type flavivirus NS1 proteins because of the insertion or deletion of 1, 2, 3, 4, 5, 6, 7, 8, 9, 10 or more amino acids not corresponding to a wild-type flavivirus NS1 protein. Moreover, the disclosure contemplates NS1 chimeras containing regions from more than two flavivirus NS1 proteins.

Other flavivirus NS1 variants of the disclosure are NS1 proteins exhibiting modified N-linked glycosylation. Flaviviruses typically contain one or two N-linked glycosylation sites as revealed by the presence of the canonical N-linked glycosylation sequence of Asparagine-any amino acid-Serine/Threonine (i.e., Asn-X-Ser/Thr). The disclosure provides flavivirus variants in which any one or more of the N-linked glycosylation site sequences of a flavivirus is altered by at least one amino acid substitution, insertion or deletion within the Asn-X-Ser/Thr sequence, mindful that substitution of a single amino acid for the amino acid corresponding to "X" does not create a NS1 variant. In particular embodiments, Zika virus variants in which the Asn-Asn-Ser sequence at positions 130-132 of Zika virus NS1 is modified are contemplated as flavivirus variants according to the disclosure. Embodiments of the disclosure include Dengue virus variants in which the Asn-Gln-Thr sequence at positions 158-160 is modified, and/or in which the Asn-Asp-Thr sequence at positions 235-237 of Dengue fever virus NS1 is modified. Embodiments of the disclosure also include Yellow fever virus variants in which the Asn-Gly-Ser sequence at positions 130-132 of Yellow fever virus NS1 is modified, and/or in which the Asn-Gly-Thr sequence at positions 208-210 of Yellow fever virus NS1 is modified.

The disclosure also provides flavivirus NS1 variants that are chimeras, as disclosed above, and that exhibit altered N-linked glycosylation, also as disclosed above. Such NS1 variants can have fragments of two or more flavivirus NS1 proteins of different serotypes or different species, and can exhibit at least one deletion or insertion of 1, 2, 3, 4, 5, 6, 7, 8, 9, 10, or more amino acids relative to any known flavivirus NS1 amino acid sequence. In addition, NS1 chimeras according to this aspect of the disclosure further contain a variant N-linked glycosylation site in which at least one canonical N-linked glycosylation site in a flavivirus NS1 protein, i.e., asparagine-any amino acid-serine or threonine (Asn-X-Ser/Thr), is modified by deletion, insertion or substitution of a non-canonical amino acid for Asn-X-Ser/Thr, mindful that the substitution of a single amino acid for the amino acid in position "X" of the canonical N-linked glycosylation site cannot produce a NS1 variant. The disclosure envisions particular embodiments in which any NS1 chimera disclosed herein also exhibits any of the particular N-linked glycosylation sequence variations or combinations of variations disclosed herein.

It is to be understood that the disclosure generally describes the NS1 protein variants, but the disclosure also comprehends polynucleotide coding regions that either express such NS1 protein variants or could be engineered to express such NS1 protein variants.

The NS1 protein variants and encoding polynucleotides of the disclosure are useful in reducing the risk of flavivirus infection by incorporating the coding region for a NS1 protein variant into the genome of a flavivirus vector such as an *Aedes* mosquito and mating such mosquitos or releasing such mosquitos in an environmental area where mating may occur to spread the variant coding region. Recognizing that mosquitos or other vector animals expressing a NS1 variant are resistant to infection by flavivirus, with time, the dissemination of the NS1 variant alleles will progressively reduce the population of vectors capable of transmitting infectious flavivirus, thereby reducing the incidence of significant viral infections and the deleterious health consequences resulting from such infections.

The following examples are presented by way of illustration and are not intended to limit the scope of the subject matter disclosed herein.

EXAMPLES

Example 1

Generation of NS1 Protein Variants

The coding regions for NS1 proteins from various flaviviruses have been isolated and such coding regions can be isolated using well-established recombinant DNA technologies, including restriction endonuclease-based DNA fragment cloning and targeted amplification technologies such as PCR. An isolated coding region for a NS1 protein, or a flavivirus genome, is amenable to mutagenesis using any known mutagenesis technique to generate the coding region for a NS1 protein variant according to the disclosure. For example, a hybrid coding region encoding a NS1 protein chimera according to the disclosure can be produced using standard recombinant DNA technologies to splice a part of the coding region of one flavivirus NS1 protein species or serotype to a part of the coding region for a different NS1 protein species or serotype.

More particularly, the DENV NS1 expression constructs encode the 16681 serotype 2 NS1 sequence preceded by the last 24 amino acids of the DENV E protein sequence, which encodes a signal sequence required for correct targeting of the NS1 sequence to the endoplasmic reticulum (ER) of the cell, and followed by the FLAG epitope tag (DYKDDDDK, SEQ ID NO:7). The amino acid sequence of the Dengue fever virus strain 16681 is available under database accession number UniProtKB P29990, incorporated herein by reference. See also, SEQ ID NOs:3 and 4. Substitutions of Asn130 to Ala130 or Asn207 to Ala207 were performed by site-directed mutagenesis, as described below.

The ZIKV NS1 expression constructs encode the Paraiba_01/2015 strain NS1 sequence preceded by the last 24 amino acids of the ZIKV E protein sequence, which encodes a signal sequence required for correct targeting of the NS1 sequence to the endoplasmic reticulum (ER) of the cell, and followed by the FLAG epitope tag (DYKDDDDK; SEQ ID NO:7). Substitutions of Asn130 to Ala130 or Asn207 to Ala207 were performed by site-directed mutagenesis (see below).

The Z-D NS1 chimera was constructed by overlap-extension PCR to fuse the N-terminal 130 amino acids of Paraiba_01/2015 ZIKV NS1 to the C-terminal portion of 16681 DENV NS1. This is preceded by the last 24 amino acids of the ZIKV E protein sequence, which encodes a signal sequence required for correct targeting of the NS1 sequence to the endoplasmic reticulum (ER) of the cell, and followed by the FLAG epitope tag (DYKDDDDK; SEQ ID NO:7).

As noted above, recombinant DNA techniques were used to effect site-directed mutagenesis of at least one codon of a canonical N-linked glycosylation site in the coding region for the Zika virus and Dengue fever virus NS1 proteins using oligonucleotide primers containing a mutation relative to the wild-type viral sequence. The effect of these mutations is to prevent N-glycosylation of the NS1 protein at that site. These mutant NS1 proteins were then expressed in a human cell line by stable transduction using a lentiviral vector. Experiments described below provide data establishing that expression of the Zika virus NS1 protein mutated at the N-glycosylation site at amino acid residue 130 (asparagine, or Asn) to alanine (Asn130Ala) does not appear to impair cell growth or viability, but potently blocks infection by dengue, Zika, and yellow fever viruses. This mutation is not found in naturally occurring strains of Zika virus. The experiments disclosed below also establish that a mutation of asparagine 207 to alanine (Asn207Ala) in the dengue virus NS1 protein blocks infection of cells by dengue and yellow fever virus.

The experimental results also indicate that the mechanism of this inhibition involves heterodimerization of the mutant NS1 protein with the wild-type NS1 protein encoded by the virus, leading to inactivation of the NS1 oligomer. One advantage of the disclosed technology is that expression of a single engineered NS1 protein from one flavivirus is able to inhibit infection by multiple flaviviruses.

Example 2

Effects of Flavivirus NS1 Chimeras

Exemplary NS1 chimeras were constructed and tested for the capacity to protect cells expressing the chimeras against wild-type flavivirus infection. In particular, Dengue fever virus and Zika virus infections of a cell line expressing a NS1 chimera were assessed. A NS1 chimera was constructed that contained Zika virus NS1 amino acids 1-130 and Dengue fever virus NS1 amino acids 131-380, i.e., the Z-D chimera. As a control, parental cell line 293T was infected with Dengue fever virus or Zika virus and the percent of infected cells were determined and the measured value was set at 100% infection. The 293T cells were also transfected with an expressible coding region for the Z-D chimera and the transfected cells were subsequently challenged with either Dengue fever virus or Zika virus. The percent infection of cells containing the transgenic Z-D chimera by either the Dengue fever virus or the Zika virus were determined and plotted in a histogram relative to the infection level of the parental 293T cells not harboring a coding region for any form of flavivirus NS1 protein.

Figure 3:
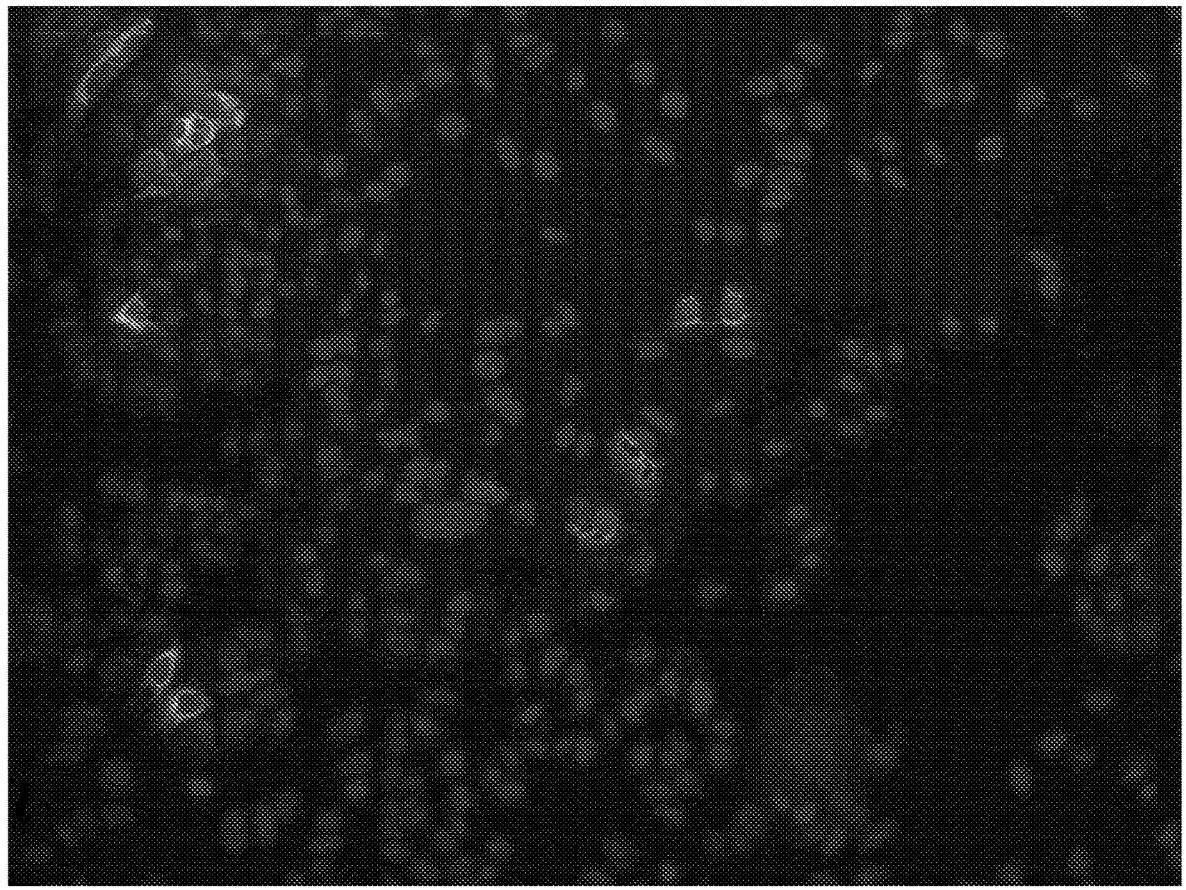
FIG. 3. Visual evidence of parental cell line Infection. Photomicrograph of stained Huh7.5.1 cells infected with wild-type Zika virus (ZIKV). Cells were fixed and immunostained for viral envelope protein using the 4G2 monoclonal antibody.
Figure 4:
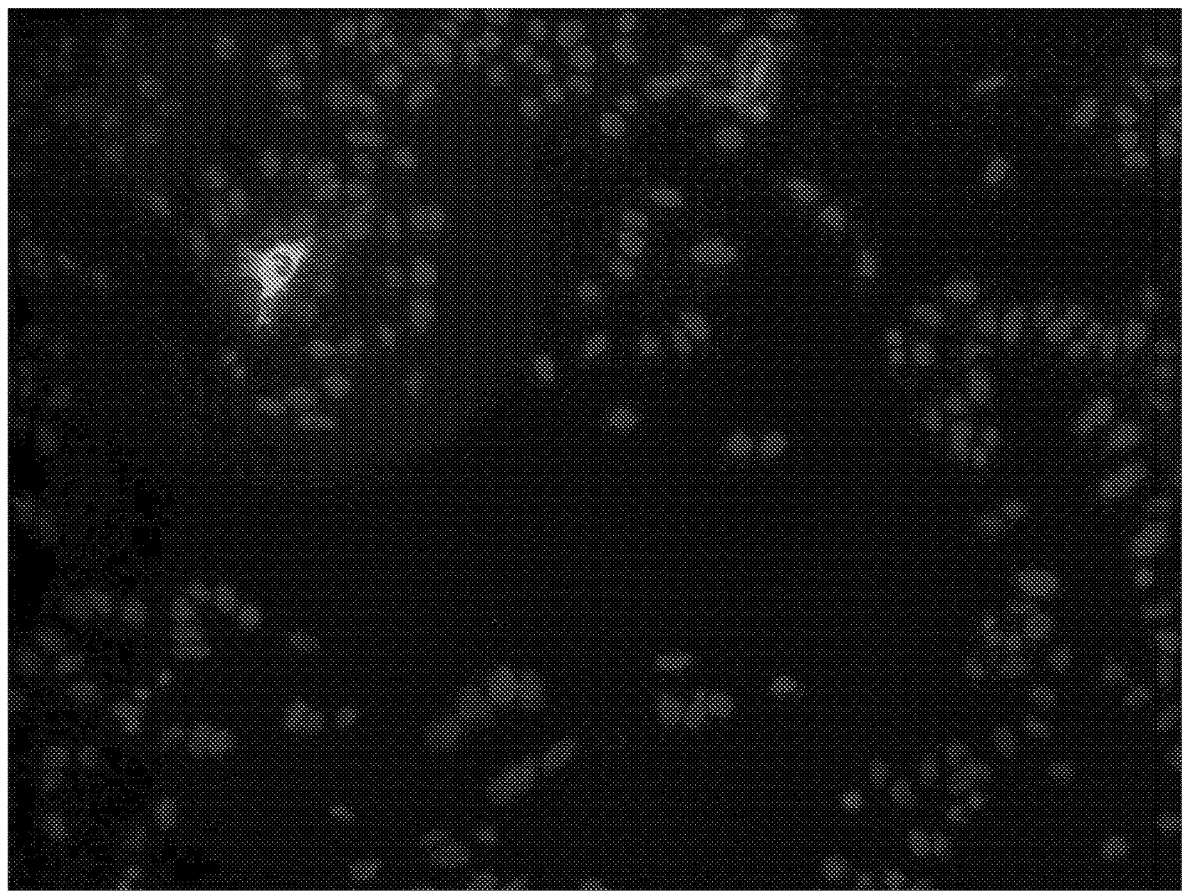
FIG. 4. Visual evidence of the Infection level of a cell line expressing the D-Z NS1 chimera. Photomicrograph of stained Huh7.5.1 cells expressing the transgenic D-Z chimera after infection with wild-type Zika virus (ZIKV). See the brief description of FIG. 2 for the structure of the D-Z chimera. Cells were fixed and immunostained for viral envelope protein using the 4G2 monoclonal antibody.
Figure 5:
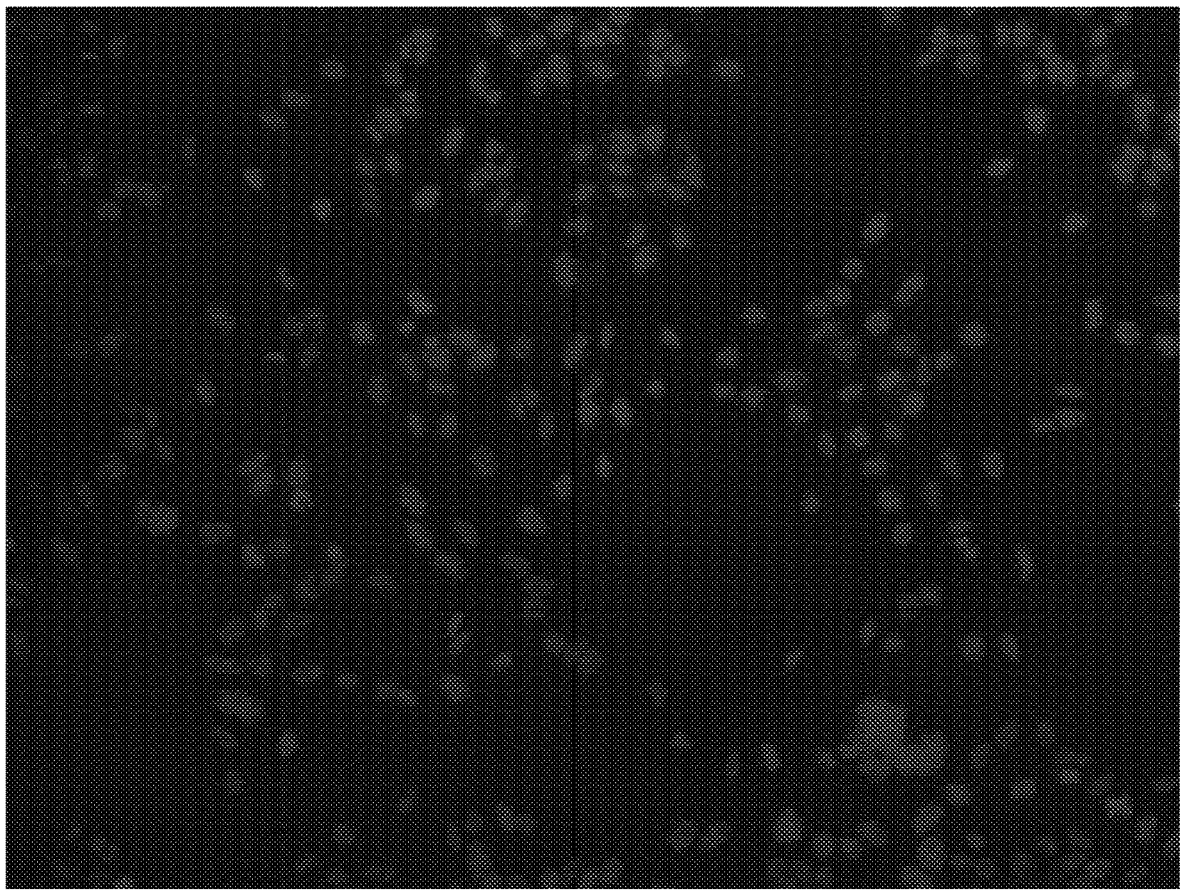
FIG. 5. Visual evidence of the Infection level of a cell line expressing the Z-D NS1 chimera. Photomicrograph of stained Huh7.5.1 cells expressing the transgenic Z-D chimera after infection with wild-type Zika virus (ZIKV). See the brief description of FIG. 2 for the structure of the Z-D chimera. Cells were fixed and immunostained for viral envelope protein using the 4G2 monoclonal antibody.
Figure 9:
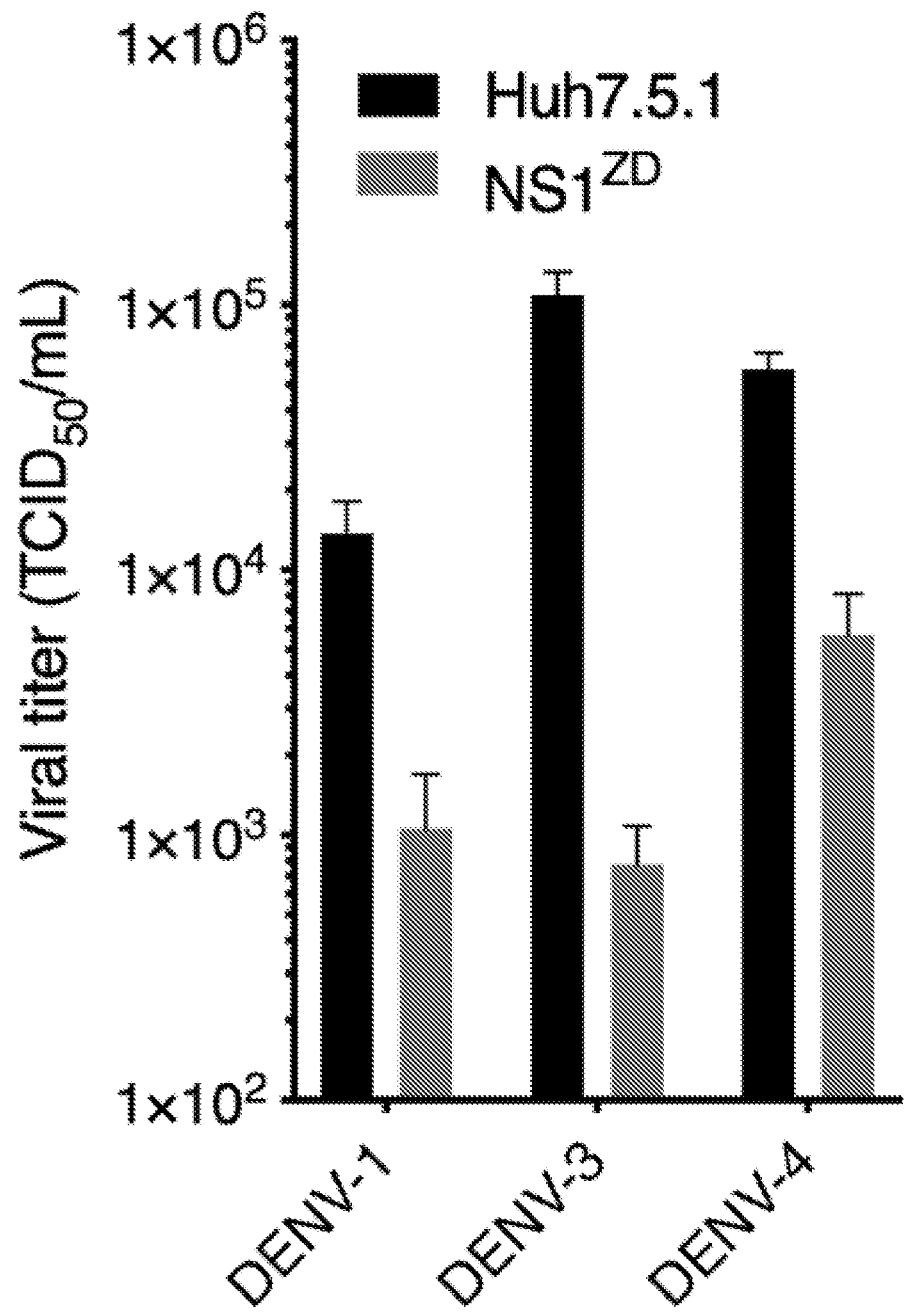
FIG. 9. Viral titers. Huh7.5.1 cells (black bars) or Huh7.5.1 cells stably expressing the Z-D NS1 chimera (red bars) were infected with the indicated serotypes of DENV. Four days after infection, viral titers in the cell culture supernatant were determined by TCID50 assay on naïve Huh7.5.1 cells. Bars indicate means+/−SD.
Figure 10:
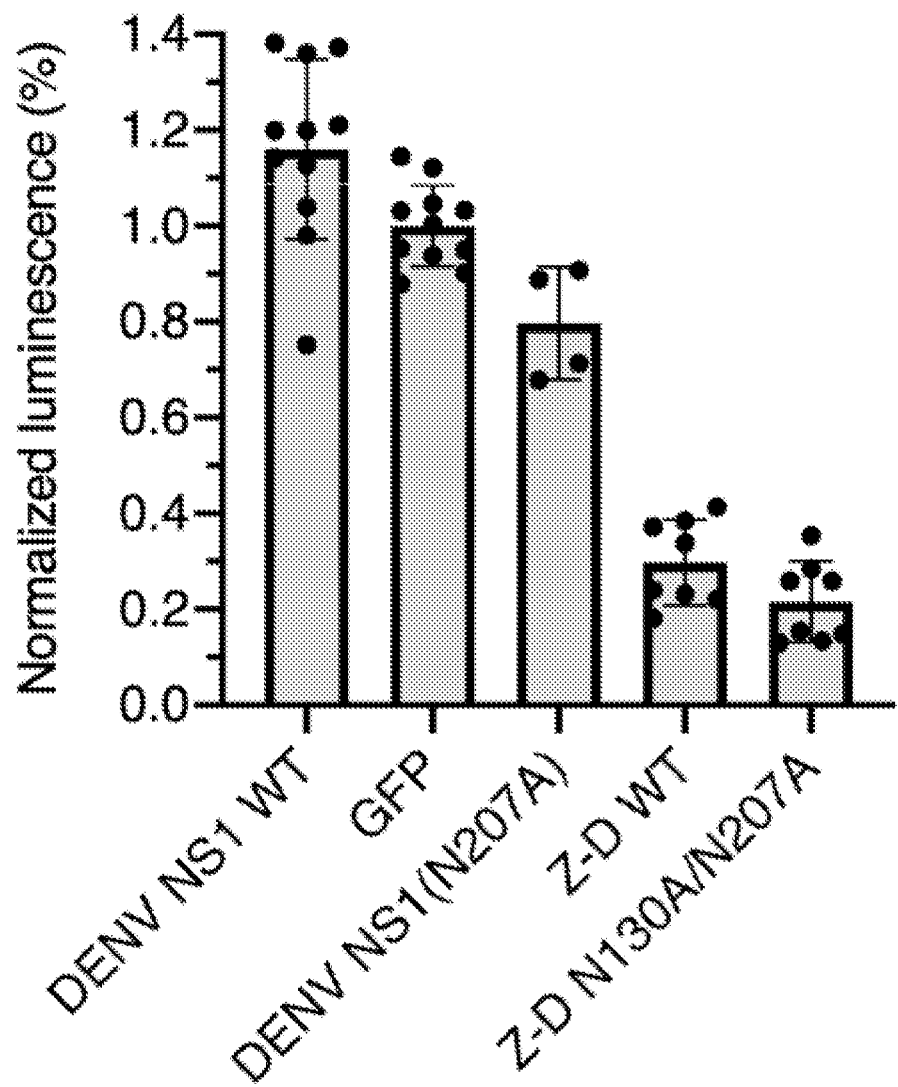
FIG. 10. Viral Infection monitored by Luciferase activity. Aag2 mosquito cells were transfected with an insect expression plasmid encoding the listed constructs and then infected with a luciferase reporter dengue virus (serotype 2, strain 16681). Four days after infection, luciferase activity was measured as a readout of viral infection. Luciferase activity was normalized to GFP-expressing cells. Bars indicate means+/−SD. The magnitude of inhibition by the Z-D NS1 constructs compared to Huh7.5.1 cells is likely due to the fact that transfection efficiency in Aag2 cells is only about 30-50%.
Figure 11:
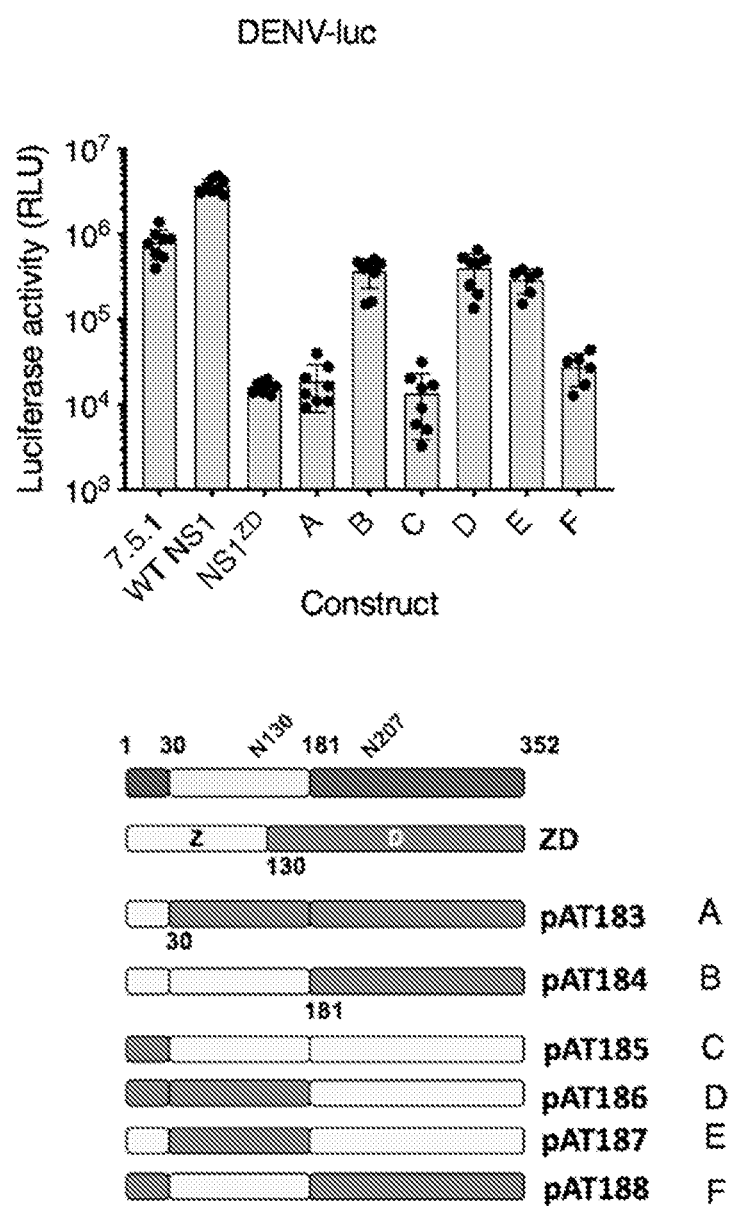
FIG. 11. Cells harboring viral chimeras. A series of NS1 chimeras was developed (constructs A through F) with different junctions between Zika (light grey) and DENV (dark grey) sequences. These constructs were stably expressed in Huh7.5.1 cells and then infected with a luciferase reporter dengue virus (serotype 2, strain 16681). Four days after infection, luciferase activity was measured as a readout of viral infection. Bars indicate means+/−SD. Constructs A and C inhibited DENV2 infection of Huh7.5.1 cells about as efficiently as the Z-D mutant.
Figure 12:
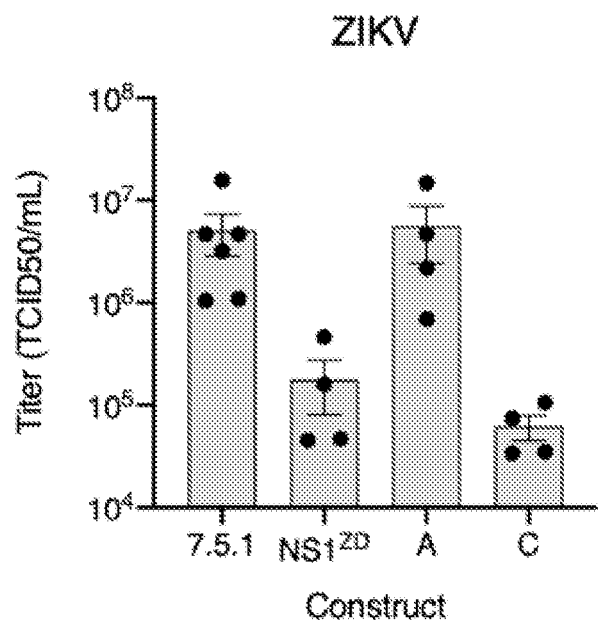
FIG. 12. Cross-species Infectivity of cells harboring viral chimeras. The series of NS1 chimeras noted in the brief description of FIG. 11 (constructs A through F), which have different junctions between Zika (light grey) and DENV (dark grey) sequences, were used in experiments to assess cross-species infectivity of cells containing viral chimeras. Huh7.5.1 cells expressing the NS1 Z-D chimera or constructs "A" or "C" were infected with ZIKV. Four days after infection, viral titers in the cell culture supernatant were determined by TCID50 assay on naïve Huh7.5.1 cells. Bars indicate means+/−SD. Construct C inhibited ZIKV infection of Huh7.5.1 cells about as efficiently as the Z-D mutant.
Figure 12:
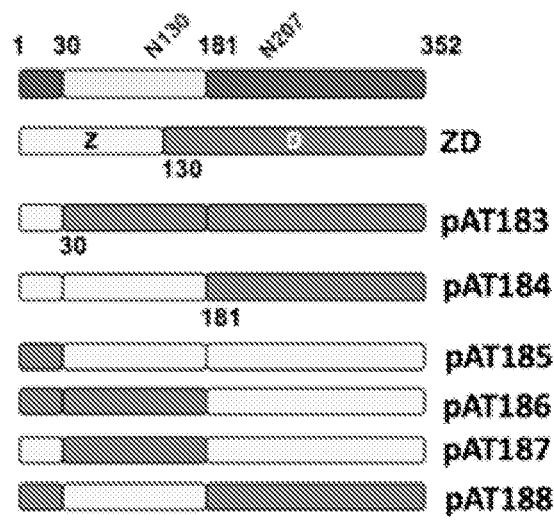

Zika virus infections of cells expressing one of two NS1 chimeras were also assessed. Mirror-image NS1 chimeras were constructed. The Z-D chimera contained amino acids 1-130 of NS1 from Zika virus and amino acids 131-380 Of Dengue fever virus NS1. The mirror-image D-Z chimera contained amino acids 1-130 of NS1 from Dengue fever virus and amino acids 131-352 of NS1 from Zika virus. Parental cell line 293T was infected with Zika virus and the percent infection was measured and set to 100% infection. The 293T cells were also transfected with a coding region for either the Z-D NS1 chimera or the D-Z NS1 chimera. Transfected cells were subsequently challenged with Zika virus and the percent infection was measured and these values are presented in histogram form as the percentage of wild-type or parental 293T cell infection level using wild-type Zika virus. Photomicrographs of parental 293T cells infected with wild-type Zika virus are shown in FIGS. 3-5, with control parental 293T cells (not expressing any NS1 chimera) infected with wild-type Zika virus are shown in FIG. 3, 293T cells expressing the NS1 D-Z chimera shown in FIG. 4, and 293T cells expressing the NS1 Z-D chimera shown in FIG. 5. The data show that the parental 293T cells are susceptible to infection by wild-type Zika virus, but the ability of wild-type Zika virus to infect such cells expressing either the NS1 D-Z or the NS1 Z-D chimera is dramatically reduced.

Example 3

Autologous Effects of Flavivirus NS1 Variants

The effect of variant, or mutant, NS1 proteins from DENV (Dengue fever virus), ZIKV (Zika virus), and YFV (Yellow fever virus) on infection were assessed by introducing the coding region for the variant NS1 protein into a host cell and then challenging that modified host cell with infectious flavivirus of the same species (or serotype). See FIG. 6. The infectious Dengue fever virus serotype 2 (DENV-2) strain 16681 full-length cDNA clone pD2/IC-30P-NBX was used to generate a *Renilla* luciferase reporter virus, as previously described (4). In the pD2/IC-30P-NBX DNA plasmid, the full-length 16681 DENV-2 cDNA clone has been cloned immediately downstream of a T7 RNA promoter and is followed by a unique XbaI restriction enzyme site at the 3' terminus of the viral cDNA to enable linearization prior to in vitro RNA transcription. That description is incorporated herein by reference. (The amino acid sequence encoded by Dengue fever virus strain 16681 is available under database accession number UniProtKB P29990, incorporated herein by reference.) Using standard published methods to generate infectious flaviviruses from plasmid DNA, linearized cDNA was transcribed in vitro with the $m^7G(5')ppp(5')A$ cap analog (New England Biolabs) using T7 Megascript (Thermo Fisher Scientific, Waltham, Mass.). This RNA was transfected into cells using TransIT mRNA reagent (Mirus Bio, Madison, Wis.) and infectious virus was harvested from the cell culture supernatant.

Additional recombinant infectious viruses included YFV-Venus, generated from pYF17D-5'C25Venus2AUbi (5), and DENV2-GFP, a 16681 strain derivative generated from pDENV2-ICP30P-A-EGFP-P2AUb (6). Descriptions of these constructs in the cited references are incorporated herein by reference. pYF17D-5'C25Venus2AUbi encodes a Venus fluorescent protein in frame after the first 25 amino acids of the YFV capsid gene, followed by a foot-and-mouth disease virus (FMDV) 2A peptide to mediate protein cleavage. This is, in turn, followed by an ubiquitin (Ubi) monomer followed by the complete YFV polyprotein sequence. DENV2-GFP encodes a GFP fluorescent protein in frame after the first 25 amino acids of the DENV capsid gene, followed by a porcine teschovirus (PTV1) 2A peptide to mediate protein cleavage. This is, in turn, followed by an ubiquitin (Ubi) monomer followed by the complete DENV polyprotein sequence. Viral stocks were generated by electroporation of in vitro transcribed RNA into WHO Vero cells for DENV2-GFP and BHK-21 cells for YFV-Venus. The ZIKV 2015 Puerto Rican PRVABC59 strain (7) was obtained from the CDC and passaged twice in Huh-7.5 human hepatoma cells. Description of the strain in the cited reference is incorporated herein by reference.

For luciferase assays, the infectious cDNA clone pD2/IC-30P-NBX encoding Dengue virus serotype 2 strain 16681 was used to construct a reporter virus and replicon. In brief, the luciferase reporter virus luc-DENV was generated by overlap extension PCR, by fusion of a Renilla luciferase (Rluc) with C-terminal self-cleaving 2A peptide to the DENV capsid in a pD2/IC-30P-NBX background, yielding a DENV-2 luciferase reporter virus. Cells were infected with the DENV-2 luciferase reporter virus (i.e., the full-length Dengue virus-2 expressing a *Renilla reniformis* luciferase reporter gene) at a multiplicity of infection (MOI)=0.1 for 2 or 3 days and luciferase activity was measured with the *Renilla* Luciferase Assay System (Promega, Madison, Wis.) and a Synergy 2 plate reader (BioTek, Winooski, Vt.). For flow cytometry assays, cells were seeded in a 24-well plate at $5 \times 10^4$ cells/well for ZIKV or at $1 \times 10^5$ cells/well for other viruses. The next day, cells were infected by incubation with flavivirus for 90 minutes at 37° C. in phosphate-buffered saline containing 2% fetal bovine serum (2% FBS-PBS). Virus inoculum was removed, fresh complete medium was added to the cells, and infections were allowed to proceed for 33 hours for YFV, and for 48 hours for DENV and ZIKV. Infected cells were detached using Accumax cell aggregate dissociation medium (eBioscience). The cells were pelleted, fixed in 2% paraformaldehyde, and permeabilized using Cytofix/Cytoperm (BD Biosciences). For ZIKV-infected cells, E-protein (envelope protein) expression was detected with the D1-4G2-4-15 monoclonal anti-envelope protein antibody (1:500 dilution; ATCC, Manassas, Va.), followed by incubation with Alexa Fluor 488-conjugated anti-mouse IgG antibody (Invitrogen) at 1:1,000 dilution. Detection of E protein was used to identify cells that were infected, as E protein is encoded by the virus and not expressed in uninfected cells. All samples were resuspended in 2% FBS-PBS. Fluorescence was monitored by fluorescence-activated cell sorting (FACS) using an LSRII flow cytometer (BD Biosciences). Data were analyzed with FlowJo software.

Figure 6:
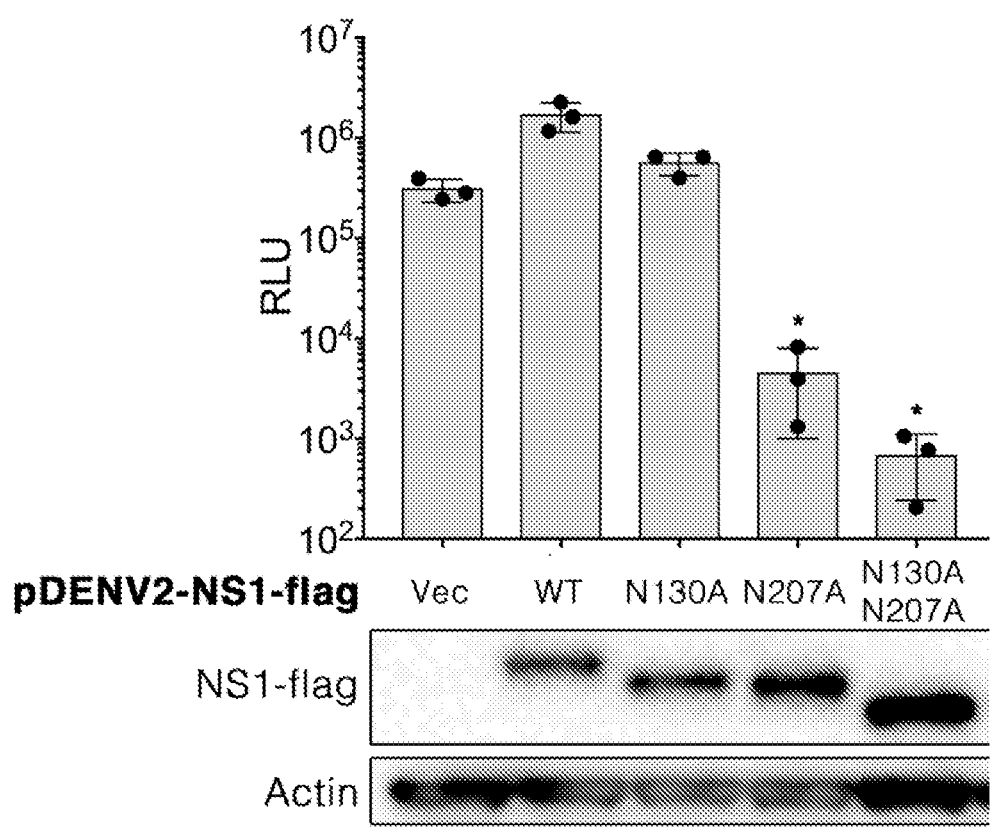

To assess the effect of NS1 protein variants on wild-type flavivirus infection of cells, Huh7.5.1 human hepatoma cells were stably transduced to express the Dengue fever virus NS1 protein having an alanine substitution for asparagine 130 (N130A), the Dengue fever virus NS1 protein having an alanine substitution for asparagine 207 (N207A), or a Dengue fever virus NS1 protein having double substitutions of N130A and N207A. The Huh7.5.1 cells were then infected with a full-length infectious DENV-2 virus expressing a *Renilla* luciferase reporter gene. Luciferase activity was measured as relative light units (RLU) for quantitation of viral infection. FIG. 6. Values are means±SD of three biological replicates. Cells were also lysed for SDS-PAGE and immunoblotting for the indicated proteins, as indicated in the middle and bottom panels of FIG. 6. The assay results shown in the histogram of FIG. 6 establish that wild-type Dengue fever virus reporter infection of Huh7.5.1 cells harboring wild-type NS1 led to infection levels about five-fold higher than when the Huh7.5.1 cells were expressing the Dengue fever virus N130A NS1 variant, and multiple orders of magnitude greater expression than Huh7.5.1 cells expressing the Dengue fever virus NS1 N207A or N130A/N207A variants. The immunoblots in the lower two panels of FIG. 6 show that NS1 was expressed in Huh7.5.1 cells expressing wild-type NS1 or any of the NS1 variants, but not in Huh7.5.1 cells simply harboring the NS1 vector, with the control immunoblot showing that actin was expressed in all Huh7.5.1 cells.

The results of this experiment establish that flavivirus NS1 variants (e.g., Dengue fever virus NS1 variants) having altered N-linked glycosylation by virtue of changes to the canonical N-linked glycosylation sequence of Asn-Xxx-Ser/Thr ("Xxx" is any amino acid) provide cells expressing such NS1 variants with protection against wild-type flavivirus (e.g., Dengue fever virus) infection.

Example 4

Heterologous Effects of Flavivirus NS1 Variants

Figure 7:
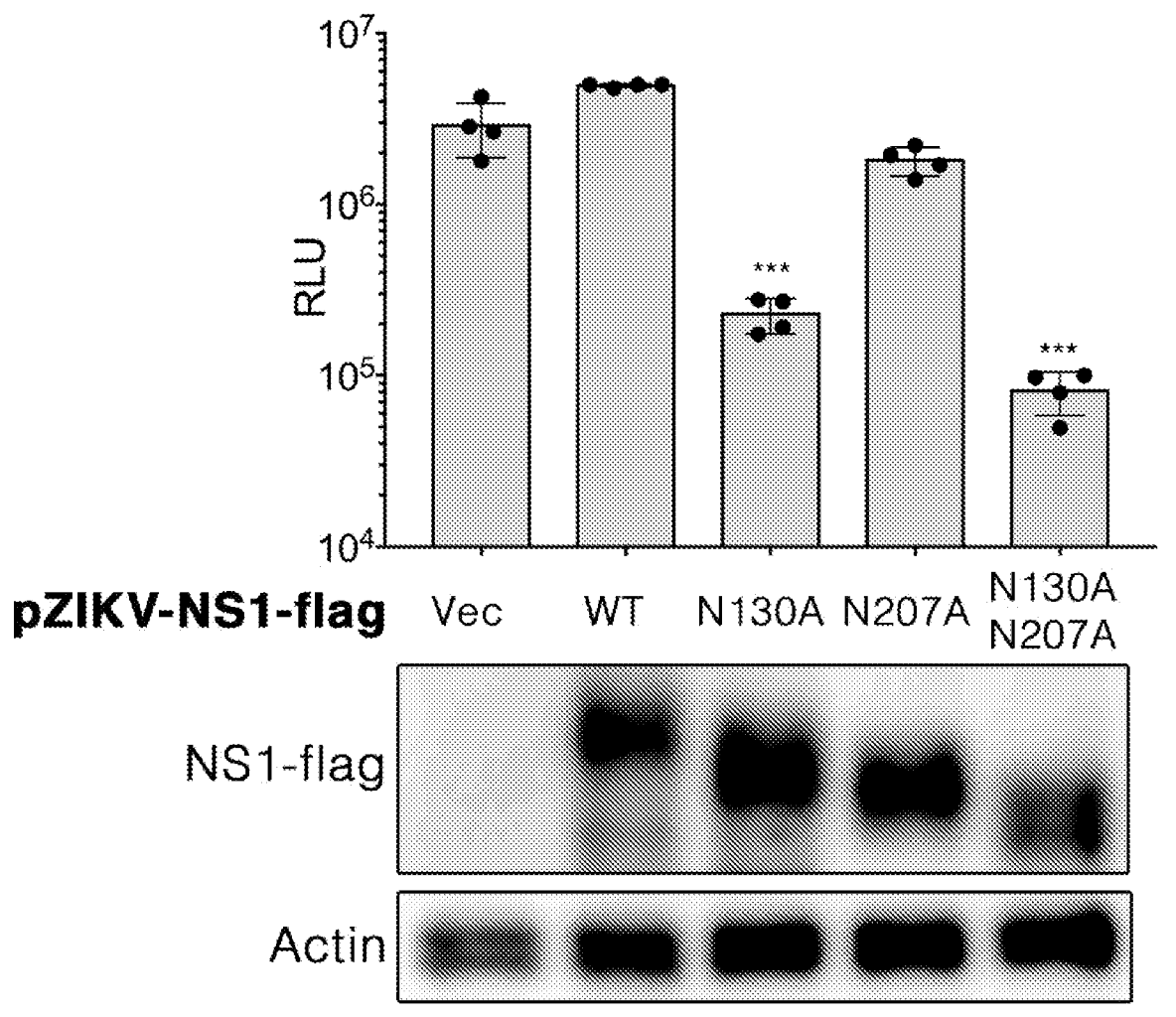

The preceding Example showed that flavivirus NS1 variants confer resistance, and hence protection against, autologous flavivirus infection, i.e., infection by the same type (species or serotype) of flavivirus as the NS1 variant. A natural extension of that demonstration was to test whether NS1 variants had broader inhibitory, or protective, effects against flavivirus infection. The question was whether a NS1 variant that conferred resistance to, and protection against, autologous flavivirus infection could also resist, or provide protection against, infection by a different type or types of flavivirus. To address that question, human hepatoma Huh7.5.1 cells were stably transduced to express the ZIKV NS1 protein variants indicated in FIG. 7 and then infected with a full-length infectious DENV-2 virus expressing a luciferase reporter gene. Luciferase activity was measured as relative light units (RLU) for quantitation of viral infection. Values are means±SD of four biological replicates. Cells were also lysed for SDS-PAGE and immunoblotting for the indicated proteins. As shown in FIG. 7, all Zika virus NS1 variants tested conferred resistance to, or protection against, Dengue fever virus infection. Those Zika virus NS1 variants, i.e., Zika virus N130A NS1 variant, Zika virus N207A NS1 variant, and Zika virus N130A/N207A NS1 variant, were modified in the canonical sequences (Asn-Xxx-Ser/Thr) for N-linked glycosylation. The data establish that modification of N-linked glycosylation sequences in the NS1 coding region of flaviviruses confers resistance to, or protection against, both autologous and heterologous wild-type flavivirus infection. FIG. 7 also provides two immunoblots showing that the NS1 variants were expressed in the Huh7.5.1 cells except for Huh7.5.1 cells only harboring vector, and that the cells were able to express the unrelated actin gene.

Example 5

Breadth of Protection Conferred by Flavivirus NS1 Variants

Figure 8:
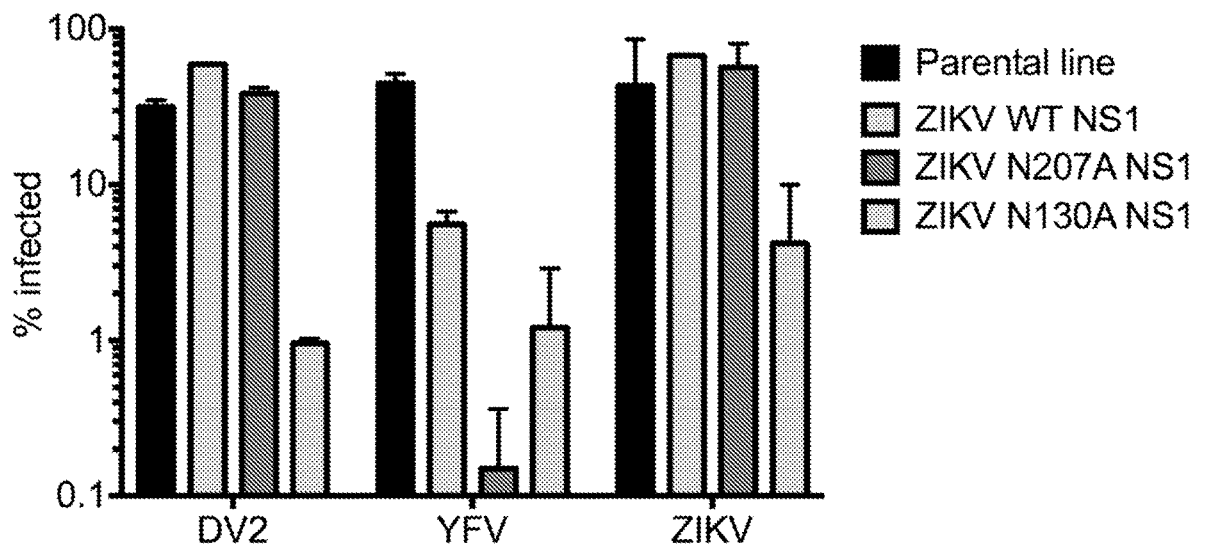

Example 3 established that flavivirus NS1 variants provided resistance to, and hence protection from, autologous flavivirus infection, i.e., infection by the wild-type flavivirus from which the NS1 variant was obtained. Example 4 expanded those findings to reveal that a given flavivirus NS1 variant could confer resistance to, and protection against, infection by a heterologous as well as the autologous flavivirus. In the experiment described in this Example, the breadth of resistance or protection was explored. Human hepatoma Huh7.5.1 cells were stably transduced to express the indicated ZIKV NS1 proteins and then infected with a full-length infectious DENV-2 virus expressing a GFP reporter, an infectious YFV virus expressing a GFP reporter, or a nonrecombinant ZIKV virus. In addition, a control was provided in the form of Huh7.5.1 cells separately infected by each of the three flaviviruses expressing a GFP reporter, but without the cells having been transduced with a coding region for any flavivirus NS1 variant (the Parental line). See FIG. 8. The percentage of infected cells was determined by flow cytometry for GFP (DV2 and YFV) or by immunostaining for the viral envelope protein (ZIKV). The results establish that disruption of either canonical N-linked glycosylation site in Zika virus NS1 confers protection against heterologous flavivirus infection. FIG. 8. The Zika virus NS1 variant N130A conferred resistance to, and hence protection against, infection by wild-type versions of all tested flaviviruses, i.e., Dengue fever virus, Yellow fever virus, and Zika virus. The Zika virus NS1 variant N207A conferred resistance to wild-type Yellow fever virus infection and, to a lesser extent, to wild-type Dengue fever virus infection, but appeared to be relatively ineffective against autologous infection by wild-type Zika virus. It is expected that this result will prove anomalous and the Zika virus NS1 variant N207A, as well as any variant that disrupts the canonical N-linked glycosylation site at either or both of Zika virus NS1 positions 130-132 and/or 207-209 will yield a NS1 variant useful in resisting infection by flavivirus.

REFERENCES

1. Huang C Y, Butrapet S, Moss K J, Childers T, Erb S M, Calvert A E, Silengo S J, Kinney R M, Blair C D, Roehrig J T. 2010. The dengue virus type 2 envelope protein fusion peptide is essential for membrane fusion. Virology 396: 305-15.
2. Tsetsarkin K A, Kenney H, Chen R, Liu G, Manukyan H, Whitehead S S, Laassri M, Chumakov K, Pletnev A G. 2016. A Full-Length Infectious cDNA Clone of Zika Virus from the 2015 Epidemic in Brazil as a Genetic Platform for Studies of Virus-Host Interactions and Vaccine Development. MBio 7.
3. Salloum S, Wang H, Ferguson C, Parton R G, Tai A W. 2013. Rab18 binds to hepatitis C virus NS5A and promotes interaction between sites of viral replication and lipid droplets. PLoS Pathog 9:e1003513.
4. Lin D L, Cherepanova N A, Bozzacco L, MacDonald M R, Gilmore R, Tai A W. 2017. Dengue Virus Hijacks a Noncanonical Oxidoreductase Function of a Cellular Oligosaccharyttransferase Complex. MBio 8(4):e00939-17.
5. Yi Z, Sperzel L, Numberger C, Bredenbeek P J, Lubick K J, Best S M, Stoyanov C T, Law L M, Yuan Z, Rice C M, MacDonald M R. 2011. Identification and characterization of the host protein DNAJC14 as a broadly active flavivirus replication modulator. PLoS Pathog 7:e1001255.
6. Schoggins J W, Dorner M, Feulner M, Imanaka N, Murphy M Y, Ploss A, Rice C M. 2012. Dengue reporter viruses reveal viral dynamics in interferon receptor-deficient mice and sensitivity to interferon effectors in vitro. Proc Nati Acad Sci USA 109:14610-5.
7. Lanciotti R S, Lambert A J, Holodniy M, Saavedra S, Signor Ldel C. 2016. Phylogeny of Zika Virus in Western Hemisphere, 2015. Emerg Infect Dis 22:933-5.

All publications and patents mentioned in the application are herein incorporated by reference in their entireties or in relevant part, as would be apparent from context. Various modifications and variations of the disclosed subject matter will be apparent to those skilled in the art without departing from the scope and spirit of the disclosure. Although the disclosure has been described in connection with specific preferred embodiments, it should be understood that the invention as claimed should not be unduly limited to such specific embodiments. Indeed, various modifications of the described modes for making or using the disclosed subject matter that are obvious to those skilled in the relevant field(s) are intended to be within the scope of the following claims.

What is claimed is:

1. A coding region for a Non-Structural Protein-1 (NS1) variant, wherein the coding region is a chimera of NS1 coding regions of at least two flavivirus species wherein two of the flavivirus species are Dengue fever virus and Zika virus, Dengue fever virus and Yellow fever virus, or Zika virus and Yellow fever virus; or wherein the coding region is both a chimera of NS1 coding regions of at least two different flavivirus species and has at least one mutation, wherein the mutation is an insertion, a deletion, or a substitution of a non-Asn codon for an Asn codon or a non-Thr codon for a Thr codon in a canonical Asn-Xxx-Ser/Thr N-linked glycosylation site, wherein Asn is asparagine, Xxx is any amino acid, and Ser/Thr is either serine or threonine.

2. The coding region of claim 1 wherein the chimera is a fusion of the NS1 coding regions of at least two flavivirus species, wherein two of the flavivirus species are Dengue fever virus and Zika virus, Dengue fever virus and Yellow fever virus, or Zika virus and Yellow fever virus.

3. The coding region of claim 2 wherein the fusion point is within or immediately adjacent to a codon for asparagine found in a canonical N-linked glycosylation site sequence of Asn-Xxx-Ser/Thr.

4. The coding region of claim 2, wherein the fusion point is at codon 130, 131, 132 of SEQ ID NOS: 2, or codon 207, 208 or 209 of SEQ ID NO: 4, or codon 208, 209, or 210 of SEQ ID NO: 6.

5. The coding region of claim 1, wherein the coding region is derived from Dengue fever virus and comprises at least one codon substitution for at least one codon encoding the amino acids corresponding to positions 130-132 of SEQ ID NO:4.

6. The coding region of claim 5, wherein the coding region comprises substitution of a codon encoding a non-asparagine amino acid for the codon encoding asparagine corresponding to position 130 of SEQ ID NO:4.

7. The coding region of claim 6, wherein the non-asparagine amino acid is alanine.

8. The coding region of claim 1, wherein the coding region is derived from Dengue fever virus and comprises substitution of a codon encoding an amino acid other than threonine for the codon encoding threonine corresponding to position 132 of SEQ ID NO:4.

9. The coding region of claim 8, wherein the non-threonine amino acid is alanine.

10. The coding region of claim 1, wherein the coding region comprises a codon substitution at one or more codons encoding amino acids corresponding to positions 207-209 of SEQ ID NO:4.

11. The coding region of claim 10 wherein an alanine codon is substituted for the asparagine codon at position 207 and/or for the threonine codon at position 209.

12. The coding region of claim 1 comprising one of the following pairs of codon substitutions:

(a) substitution of a non-asparagine codon for the codon encoding the asparagine corresponding to position 130 of SEQ ID NO:4 and substitution of a non-asparagine codon for the codon encoding the asparagine corresponding to position 207 of SEQ ID NO:4;

(b) substitution of a non-asparagine codon for the codon encoding the asparagine corresponding to position 130 of SEQ ID NO:4 and substitution of a non-threonine codon for the codon encoding the threonine corresponding to position 209 of SEQ ID NO:4;

(c) substitution of a non-threonine codon for the codon encoding the threonine corresponding to position 132 of SEQ ID NO:4 and substitution of a non-asparagine codon for the codon encoding the asparagine corresponding to position 207 of SEQ ID NO:4; or (d) substitution of a non-threonine codon for the codon encoding the threonine corresponding to position 132 of SEQ ID NO:4 and substitution of a non-threonine codon for the codon encoding the threonine corresponding to position 209 of SEQ ID NO:4.

13. The coding region of claim 1, wherein the coding region is derived from Yellow fever virus and wherein the coding region comprises a codon substitution at one or more codons encoding amino acids corresponding to positions 130-132 of SEQ ID NO:6.

14. The coding region of claim 13, wherein the coding region comprises substitution of an alanine codon for the codon encoding the asparagine corresponding to position 130 of SEQ ID NO:6 and/or for the codon encoding the serine corresponding to position 132 of SEQ ID NO:6.

15. The coding region of claim 1, wherein the coding region comprises a codon substitution at one or more codons encoding amino acids corresponding to positions 208-210 of SEQ ID NO:6.

16. The coding region of claim 15 wherein the coding region comprises substitution of an alanine codon for the codon encoding the asparagine corresponding to position 208 of SEQ ID NO:6 and/or for the codon encoding the threonine corresponding to position 210 of SEQ ID NO:6.

17. The coding region of claim 1 comprising one of the following pairs of codon substitutions:

(a) substitution of a non-asparagine codon for the codon encoding the asparagine corresponding to position 130 of SEQ ID NO:6 and substitution of a non-asparagine codon for the codon encoding the asparagine corresponding to position 208 of SEQ ID NO:6;

(b) substitution of a non-asparagine codon for the codon encoding the asparagine corresponding to position 130 of SEQ ID NO:6 and substitution of a non-threonine codon for the codon encoding the threonine corresponding to position 210 of SEQ ID NO:6;

(c) substitution of a non-serine codon for the codon encoding the serine corresponding to position 132 of SEQ ID NO:6 and substitution of a non-asparagine codon for the codon encoding the asparagine corresponding to position 208 of SEQ ID NO:6; or (d) substitution of a non-serine codon for the codon encoding the serine corresponding to position 132 of SEQ ID NO:6 and substitution of a non-threonine codon for the codon encoding the threonine corresponding to position 210 of SEQ ID NO:6.

18. The coding region of claim 1, wherein the coding region is derived from Zika virus and comprises a codon substitution at one or more codons encoding amino acids corresponding to positions 130-132 of SEQ ID NO:2.

19. The coding region of claim 18, wherein the coding region comprises substitution of an alanine codon for the codon encoding the asparagine corresponding to position 130 of SEQ ID NO:2 and/or for the codon encoding the serine corresponding to position 132 of SEQ ID NO:2.

20. The NS1 protein variant encoded by the coding region of claim 1.

21. The NS1 protein variant of claim 20 wherein the NS1 protein variant is encoded by the coding region derived from Dengue fever virus, Yellow fever virus, or Zika virus.

22. A method of reducing the risk of flavivirus infection in a subject comprising administering an effective amount of the coding region of claim 1.

23. The method of claim 22 wherein the coding region for a flavivirus NS1 protein variant is derived from at least two of Dengue fever NS1 protein, Yellow fever NS1 protein, or Zika virus NS1 protein.

24. A method of reducing the risk of flavivirus infection in a population of humans comprising:
  (a) introducing a coding region of claim 1 into a mosquito vector for flavivirus;
  (b) breeding the mosquito vector; and
  (c) releasing the mosquito vector into an environment inhabited by humans, whereby the mosquito vector breeds with wild-type mosquitos of the same species, thereby disseminating the coding region for the NS1 protein variant to reduce the risk of flavivirus infection in the humans.

25. The method of claim 24 wherein the coding region for the flavivirus NS1 protein variant is derived from the coding region for Dengue fever virus, Yellow fever virus, or Zika virus.

* * * * *

UNITED STATES PATENT AND TRADEMARK OFFICE
CERTIFICATE OF CORRECTION

PATENT NO. : 11,702,453 B2  
APPLICATION NO. : 17/269191  
DATED : July 18, 2023  
INVENTOR(S) : Andrew Tai et al.

Page 1 of 1

It is certified that error appears in the above-identified patent and that said Letters Patent is hereby corrected as shown below:

On the Title Page

At item (73), Line 1, "REGENTS" should be -- THE REGENTS --.

Signed and Sealed this
First Day of October, 2024

Katherine Kelly Vidal
*Director of the United States Patent and Trademark Office*

SEQUENCE LISTING

```
<160> NUMBER OF SEQ ID NOS: 7

<210> SEQ ID NO 1
<211> LENGTH: 1056
<212> TYPE: DNA
<213> ORGANISM: Zika Virus
<220> FEATURE:
<221> NAME/KEY: misc_feature
<223> OTHER INFORMATION: Zika virus NS1 polynucleotide sequence

<400> SEQUENCE: 1
gatgtggggt gctcggtgga cttctcaaag aaggagacga gatgcggtac aggggtgttc      60
gtctataacg acgttgaagc ctggagggac aggtacaagt accatcctga ctccccccgt     120
agattggcag cagcagtcaa gcaagcctgg gaagatggta tctgcgggat ctcctctgtt     180
tcaagaatgg aaaacatcat gtggagatca gtagaagggg agctcaacgc aatcctggaa     240
gagaatggag ttcaactgac ggtcgttgtg ggatctgtaa aaaaccccat gtggagaggt     300
ccacagagat tgcccgtgcc tgtgaacgag ctgccccacg gctggaaggc ttggggggaaa    360 tcgtacttcg tcagagcagc aaagacaaat aacagctttg tcgtggatgg tgacacactg    420
```

```
aaggaatgcc cactcaaaca tagagcatgg aacagctttc ttgtggagga tcatgggttc    480
ggggtatttc acactagtgt ctggctcaag gttagagaag attattcatt agagtgtgat    540
ccagccgtta ttggaacagc tgttaaggga aaggaggctg tacacagtga tctaggctac    600
tggattgaga gtgagaagaa tgacacatgg aggctgaaga gggcccacct gatcgagatg    660
aaaacatgtg aatggccaaa gtcccacaca ttgtggacag atggaataga agagagtgat    720
ctgatcatac ccaagtctttt agctgggcca ctcagccatc acaataccag agagggctac    780
aggacccaaa tgaaagggcc atggcacagt gaagagcttg aaattcggtt tgaggaatgc    840
ccaggcacta aggtccacgt ggaggaaaca tgtggaacaa gaggaccatc tctgagatca    900
accactgcaa gcggaagggt gatcgaggaa tggtgctgca gggagtgcac aatgcccca    960 ctgtcgttcc gggctaaaga tggctgttgg tatggaatgg agataaggcc caggaaagaa   1020
ccagaaagca acttagtaag gtcagtggtg actgca                             1056
```

<210> SEQ ID NO 2
<211> LENGTH: 352
<212> TYPE: PRT
<213> ORGANISM: Zika Virus
<220> FEATURE:
<221> NAME/KEY: MISC_FEATURE
<223> OTHER INFORMATION: NS1 amino acid sequence
<220> FEATURE:
<221> NAME/KEY: MISC_FEATURE
<222> LOCATION: (130)..(132)
<223> OTHER INFORMATION: N-linked glycosylation site
<220> FEATURE:
<221> NAME/KEY: MISC_FEATURE
<222> LOCATION: (207)..(209)
<223> OTHER INFORMATION: N-linked glycosylation site

<400> SEQUENCE: 2

```
Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
            20                  25                  30

Lys Tyr His Pro Asp Ser Pro Arg Arg Leu Ala Ala Ala Val Lys Gln
        35                  40                  45

Ala Trp Glu Asp Gly Ile Cys Gly Ile Ser Ser Val Ser Arg Met Glu
    50                  55                  60

Asn Ile Met Trp Arg Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
        115                 120                 125

Thr Asn Asn Ser Phe Val Val Asp Gly Asp Thr Leu Lys Glu Cys Pro
    130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Lys Glu
            180                 185                 190

Ala Val His Ser Asp Leu Gly Tyr Trp Ile Glu Ser Glu Lys Asn Asp
```

```
        195                 200                 205

Thr Trp Arg Leu Lys Arg Ala His Leu Ile Glu Met Lys Thr Cys Glu
    210                 215                 220

Trp Pro Lys Ser His Thr Leu Trp Thr Asp Gly Ile Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Met Lys Gly Pro Trp His Ser Glu Glu
            260                 265                 270

Leu Glu Ile Arg Phe Glu Glu Cys Pro Gly Thr Lys Val His Val Glu
        275                 280                 285

Glu Thr Cys Gly Thr Arg Gly Pro Ser Leu Arg Ser Thr Thr Ala Ser
    290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Val Val Thr Ala
            340                 345                 350

<210> SEQ ID NO 3
<211> LENGTH: 1056
<212> TYPE: DNA
<213> ORGANISM: Dengue Fever virus NS1
<220> FEATURE:
<221> NAME/KEY: misc_feature
<223> OTHER INFORMATION: Dengue virus NS1
<220> FEATURE:
<221> NAME/KEY: misc_feature
<223> OTHER INFORMATION: Dengue Virus Type 2
<220> FEATURE:
<221> NAME/KEY: misc_feature
<223> OTHER INFORMATION: 16681 strain

<400> SEQUENCE: 3
gatagtggtt gcgttgtgag ctggaaaaac aaagaactga aatgtggcag tgggattttc     60
atcacagaca acgtgcacac atggacagaa caatacaagt tccaaccaga atccccttca    120
aaactagctt cagctatcca gaaagcccat gaagagggca tttgtggaat ccgctcagta    180
acaagactgg agaatctgat gtggaaacaa ataacaccag aattgaatca cattctatca    240
gaaaatgagg tgaagttaac tattatgaca ggagacatca aaggaatcat gcaggcagga    300
aaacgatctc tgcggcctca gcccactgag ctgaagtatt catggaaaac atggggcaaa    360
gcaaaaatgc tctctacaga gtctcataac cagacctttc tcattgatgg ccccgaaaca    420
gcagaatgcc ccaacacaaa tagagcttgg aattcgttgg aagttgaaga ctatggcttt    480
ggagtattca ccaccaatat atggctaaaa ttgaaagaaa aacaggatgt attctgcgac    540
tcaaaactca tgtcagcggc cataaaagac aacagagccg tccatgccga tatgggttat    600
tggatagaaa gtgcactcaa tgacacatgg aagatagaga aagcctcttt cattgaagtt    660
aaaaactgcc actggccaaa atcacacacc ctctggagca atggagtgct agaaagtgag    720
atgataattc caaagaatct cgctggacca gtgtctcaac acaactatag accaggctac    780
catacacaaa taacaggacc atggcatcta ggtaagcttg agatggactt tgatttctgt    840
gatggaacaa cagtggtagt gactgaggac tgcggaaata gaggaccctc tttgagaaca    900
accactgcct ctggaaaact cataacagaa tggtgctgcc gatcttgcac attaccaccg    960
ctaagataca gaggtgagga tgggtgctgg tacgggatgg aaatcagacc attgaaggag   1020
```
aaagaagaga atttggtcaa ctccttggtc acagct        1056

<210> SEQ ID NO 4
<211> LENGTH: 352
<212> TYPE: PRT
<213> ORGANISM: Dengue Fever virus NS1
<220> FEATURE:
<221> NAME/KEY: MISC_FEATURE
<223> OTHER INFORMATION: Dengue virus NS1
<220> FEATURE:
<221> NAME/KEY: MISC_FEATURE
<222> LOCATION: (130)..(132)
<223> OTHER INFORMATION: N-linked glycosylation site
<220> FEATURE:
<221> NAME/KEY: MISC_FEATURE
<222> LOCATION: (207)..(209)
<223> OTHER INFORMATION: N-linked glycosylation site

<400> SEQUENCE: 4

```
Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
            20                  25                  30

Lys Phe Gln Pro Glu Ser Pro Ser Lys Leu Ala Ser Ala Ile Gln Lys
        35                  40                  45

Ala His Glu Glu Gly Ile Cys Gly Ile Arg Ser Val Thr Arg Leu Glu
    50                  55                  60

Asn Leu Met Trp Lys Gln Ile Thr Pro Glu Leu Asn His Ile Leu Ser
65                  70                  75                  80

Glu Asn Glu Val Lys Leu Thr Ile Met Thr Gly Asp Ile Lys Gly Ile
                85                  90                  95

Met Gln Ala Gly Lys Arg Ser Leu Arg Pro Gln Pro Thr Glu Leu Lys
            100                 105                 110

Tyr Ser Trp Lys Thr Trp Gly Lys Ala Lys Met Leu Ser Thr Glu Ser
        115                 120                 125

His Asn Gln Thr Phe Leu Ile Asp Gly Pro Glu Thr Ala Glu Cys Pro
    130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Lys Glu Lys Gln Asp
                165                 170                 175

Val Phe Cys Asp Ser Lys Leu Met Ser Ala Ala Ile Lys Asp Asn Arg
            180                 185                 190

Ala Val His Ala Asp Met Gly Tyr Trp Ile Glu Ser Ala Leu Asn Asp
        195                 200                 205

Thr Trp Lys Ile Glu Lys Ala Ser Phe Ile Glu Val Lys Asn Cys His
    210                 215                 220

Trp Pro Lys Ser His Thr Leu Trp Ser Asn Gly Val Leu Glu Ser Glu
225                 230                 235                 240

Met Ile Ile Pro Lys Asn Leu Ala Gly Pro Val Ser Gln His Asn Tyr
                245                 250                 255

Arg Pro Gly Tyr His Thr Gln Ile Thr Gly Pro Trp His Leu Gly Lys
            260                 265                 270

Leu Glu Met Asp Phe Asp Phe Cys Asp Gly Thr Thr Val Val Val Thr
        275                 280                 285

Glu Asp Cys Gly Asn Arg Gly Pro Ser Leu Arg Thr Thr Thr Ala Ser
    290                 295                 300
```

```
Gly Lys Leu Ile Thr Glu Trp Cys Cys Arg Ser Cys Thr Leu Pro Pro
305                 310                 315                 320

Leu Arg Tyr Arg Gly Glu Asp Gly Cys Trp Tyr Gly Met Glu Ile Arg
                325                 330                 335

Pro Leu Lys Glu Lys Glu Glu Asn Leu Val Asn Ser Leu Val Thr Ala
            340                 345                 350

<210> SEQ ID NO 5
<211> LENGTH: 1227
<212> TYPE: DNA
<213> ORGANISM: Yellow Fever virus NS1
<220> FEATURE:
<221> NAME/KEY: misc_feature
<223> OTHER INFORMATION: Yellow Fever NS1
<220> FEATURE:
<221> NAME/KEY: misc_feature
<223> OTHER INFORMATION: 17D vaccine strain

<400> SEQUENCE: 5
gatcaaggat gcgccatcaa ctttggcaag agagagctca agtgcggaga tggtatcttc      60
atatttagag actctgatga ctggctgaac aagtactcat actatccaga agatcctgtg    120
aagcttgcat caatagtgaa agcctctttt gaagaaggga agtgtggcct aaattcagtt    180
gactcccttg agcatgagat gtggagaagc agggcagatg agatcaatgc cattttgag     240
gaaaacgagg tggacatttc tgttgtcgtg caggatccaa agaatgttta ccagagagga    300
actcatccat tttccagaat tcgggatggt ctgcagtatg gttggaagac ttggggtaag    360
aaccttgtgt tctccccagg gaggaagaat ggaagcttca tcatagatgg aaagtccagg    420
aaagaatgcc cgttttcaaa ccgggtctgg aattcttctcc agatagagga gtttgggacg   480
ggagtgttca ccacacgcgt gtacatggac gcagtctttg aatacaccat agactgcgat    540
ggatctatct gggtgcagc ggtgaacgga aaaaagagtg cccatggctc tccaacattt     600
tggatgggaa gtcatgaagt aaatgggaca tggatgatcc acaccttgga ggcattagat    660
tacaaggagt gtgagtggcc actgacacat acgattggaa catcagttga agagagtgaa    720
atgttcatgc cgagatcaat cggaggccca gttagctctc acaatcatat ccctggatac    780
aaggttcaga cgaacggacc ttggatgcag gtaccactag aagtgaagag agaagcttgc    840
ccagggacta gcgtgatcat tgatggcaac tgtgatggac ggggaaaatc aaccagatcc    900
accacggata gcgggaaagt tattcctgaa tggtgttgcc gctcctgcac aatgccgcct    960
gtgagcttcc atggtagtga tgggtgttgg tatcccatgg aaattaggcc aaggaaaacg   1020
catgaaagcc atctggtgcg ctcctgggtt acagctggag aaatacatgc tgtccctttt   1080
ggtttggtga gcatgatgat agcaatggaa gtggtcctaa ggaaaagaca gggaccaaag   1140
caaatgttgg ttggaggagt agtgctcttg ggagcaatgc tggtcgggca agtaactctc   1200
cttgatttgc tgaaactcac agtggct                                       1227

<210> SEQ ID NO 6
<211> LENGTH: 352
<212> TYPE: PRT
<213> ORGANISM: Yellow Fever virus NS1
<220> FEATURE:
<221> NAME/KEY: MISC_FEATURE
<223> OTHER INFORMATION: Yellow Fever NS1
<220> FEATURE:
<221> NAME/KEY: MISC_FEATURE
<222> LOCATION: (130)..(132)
<223> OTHER INFORMATION: N-linked glycosylation site
<220> FEATURE:
<221> NAME/KEY: MISC_FEATURE
```

<222> LOCATION: (208)..(210)
<223> OTHER INFORMATION: N-linked glycosylation site

<400> SEQUENCE: 6

```
Asp Gln Gly Cys Ala Ile Asn Phe Gly Lys Arg Glu Leu Lys Cys Gly
1               5                   10                  15
Asp Gly Ile Phe Ile Phe Arg Asp Ser Asp Asp Trp Leu Asn Lys Tyr
            20                  25                  30
Ser Tyr Tyr Pro Glu Asp Pro Val Lys Leu Ala Ser Ile Val Lys Ala
        35                  40                  45
Ser Phe Glu Glu Gly Lys Cys Gly Leu Asn Ser Val Asp Ser Leu Glu
    50                  55                  60
His Glu Met Trp Arg Ser Arg Ala Asp Glu Ile Asn Ala Ile Phe Glu
65                  70                  75                  80
Glu Asn Glu Val Asp Ile Ser Val Val Gln Asp Pro Lys Asn Val
                85                  90                  95
Tyr Gln Arg Gly Thr His Pro Phe Ser Arg Ile Arg Asp Gly Leu Gln
            100                 105                 110
Tyr Gly Trp Lys Thr Trp Gly Lys Asn Leu Val Phe Ser Pro Gly Arg
        115                 120                 125
Lys Asn Gly Ser Phe Ile Ile Asp Gly Lys Ser Arg Lys Glu Cys Pro
    130                 135                 140
Phe Ser Asn Arg Val Trp Asn Ser Phe Gln Ile Glu Glu Phe Gly Thr
145                 150                 155                 160
Gly Val Phe Thr Thr Arg Val Tyr Met Asp Ala Val Phe Glu Tyr Thr
                165                 170                 175
Ile Asp Cys Asp Gly Ser Ile Leu Gly Ala Ala Val Asn Gly Lys Lys
            180                 185                 190
Ser Ala His Gly Ser Pro Thr Phe Trp Met Gly Ser His Glu Val Asn
        195                 200                 205
Gly Thr Trp Met Ile His Thr Leu Glu Ala Leu Asp Tyr Lys Glu Cys
    210                 215                 220
Glu Trp Pro Leu Thr His Thr Ile Gly Thr Ser Val Glu Glu Ser Glu
225                 230                 235                 240
Met Phe Met Pro Arg Ser Ile Gly Gly Pro Val Ser Ser His Asn His
                245                 250                 255
Ile Pro Gly Tyr Lys Val Gln Thr Asn Gly Pro Trp Met Gln Val Pro
            260                 265                 270
Leu Glu Val Lys Arg Glu Ala Cys Pro Gly Thr Ser Val Ile Ile Asp
        275                 280                 285
Gly Asn Cys Asp Gly Arg Gly Lys Ser Thr Arg Ser Thr Thr Asp Ser
    290                 295                 300
Gly Lys Val Ile Pro Glu Trp Cys Cys Arg Ser Cys Thr Met Pro Pro
305                 310                 315                 320
Val Ser Phe His Gly Ser Asp Gly Cys Trp Tyr Pro Met Glu Ile Arg
                325                 330                 335
Pro Arg Lys Thr His Glu Ser His Leu Val Arg Ser Trp Val Thr Ala
            340                 345                 350
```

<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: MISC_FEATURE
<223> OTHER INFORMATION: NS1-flag protein

<400> SEQUENCE: 7

Asp Tyr Lys Asp Asp Asp Asp Lys
1               5
```